US012679865B2

(12) United States Patent
Callahan et al.

(10) Patent No.: US 12,679,865 B2
(45) Date of Patent: Jul. 14, 2026

(54) METHODS FOR MAKING STABLE PROTEIN COMPOSITIONS

(71) Applicant: AMGEN INC., Thousand Oaks, CA (US)

(72) Inventors: William Callahan, Thousand Oaks, CA (US); Lorenzo Desantiago, Valencia, CA (US); Clea Talley, Camarillo, CA (US); Yael Wexler-Cohen, Thousand Oaks, CA (US); Jeffrey Abel, Simi Valley, CA (US); Rahul Kaushik, Newbury Park, CA (US); Nitya Mariam Jacob, Thousand Oaks, CA (US); Carson Tran, Sherman Oaks, CA (US); Nicole Ball, Thousand Oaks, CA (US); Monica Goss, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 963 days.

(21) Appl. No.: 17/046,662

(22) PCT Filed: Mar. 28, 2019

(86) PCT No.: PCT/US2019/024683
§ 371 (c)(1),
(2) Date: Oct. 9, 2020

(87) PCT Pub. No.: WO2019/199476
PCT Pub. Date: Oct. 17, 2019

(65) Prior Publication Data
US 2021/0163531 A1 Jun. 3, 2021

Related U.S. Application Data

(60) Provisional application No. 62/656,687, filed on Apr. 12, 2018.

(51) Int. Cl.
| | |
|---|---|
| C07K 1/18 | (2006.01) |
| C07K 1/16 | (2006.01) |
| C07K 1/34 | (2006.01) |
| C07K 1/36 | (2006.01) |
| C07K 14/505 | (2006.01) |
| C07K 14/535 | (2006.01) |
| C07K 14/71 | (2006.01) |
| C07K 14/715 | (2006.01) |
| C07K 16/18 | (2006.01) |
| C07K 16/22 | (2006.01) |
| C07K 16/28 | (2006.01) |
| C07K 16/30 | (2006.01) |
| C07K 16/32 | (2006.01) |
| C07K 16/40 | (2006.01) |

(52) U.S. Cl.
CPC ............... *C07K 1/36* (2013.01); *C07K 1/165* (2013.01); *C07K 1/18* (2013.01); *C07K 1/34* (2013.01); *C07K 14/505* (2013.01); *C07K 14/535* (2013.01); *C07K 14/71* (2013.01); *C07K 14/7151* (2013.01); *C07K 16/18* (2013.01); *C07K 16/22* (2013.01); *C07K 16/2803* (2013.01); *C07K 16/2809* (2013.01); *C07K 16/2863* (2013.01); *C07K 16/2869* (2013.01); *C07K 16/2875* (2013.01); *C07K 16/2878* (2013.01); *C07K 16/3069* (2013.01); *C07K 16/32* (2013.01); *C07K 16/40* (2013.01); *C07K 2317/31* (2013.01)

(58) Field of Classification Search
CPC ...................................................... C07K 1/36
See application file for complete search history.

(56) References Cited

U.S. PATENT DOCUMENTS

| | | | |
|---|---|---|---|
| 9,458,241 B2 | 10/2016 | Bhat et al. | |
| 2006/0051347 A1* | 3/2006 | Winter .................... | C07K 1/34 530/387.3 |
| 2009/0005542 A1* | 1/2009 | Turecek ................. | A61K 47/61 548/546 |
| 2010/0278822 A1* | 11/2010 | Fraunhofer ...... | A61K 39/39591 424/133.1 |
| 2012/0009650 A1* | 1/2012 | Koepf .................. | C12N 9/6435 530/380 |
| 2013/0195888 A1* | 8/2013 | Wang .............. | A61K 39/39591 530/389.1 |
| 2014/0113355 A1 | 4/2014 | Ristol Debart et al. | |
| 2015/0133644 A1 | 5/2015 | Bruckschwaiger et al. | |
| 2016/0347833 A1* | 12/2016 | Jensen ................ | C07K 16/244 |
| 2017/0143828 A1 | 5/2017 | Fraunhofer et al. | |
| 2017/0355729 A1 | 12/2017 | Westoby et al. | |
| 2019/0292221 A1* | 9/2019 | Abrantes ................. | C07K 1/34 |
| 2022/0177555 A1* | 6/2022 | Blanchetot ............. | C07K 16/18 |

(Continued)

FOREIGN PATENT DOCUMENTS

| | | |
|---|---|---|
| JP | 11-509525 | 8/1999 |
| JP | 2011/518110 A | 6/2011 |

(Continued)

OTHER PUBLICATIONS

Abel et al., A Small-Scale Process for Predicting Donnan and Volume Exclusion Effects During Ultrafiltration/Diafiltration Process Development, J. Pharm. Sci., 107(5):1296-1303 (2018).
Fekete et al., Theory and practice of size exclusion chromatography for the analysis of protein aggregates, Journal of Pharmaceutical and Biomedical Analysis, 101:161-173 (2014).
Gail, Virus Inactivation in the 1990s and into the 21 st Century, Part 4, Culture media, Biotechnology Products, and Vaccines, Biopharm International., 50-57 (2003).

(Continued)

*Primary Examiner* — Suzanne M Noakes

(74) *Attorney, Agent, or Firm* — MARSHALL, GERSTEIN & BORUN LLP

(57) ABSTRACT

The invention relates to methods for preparing stable buffered and buffer-free protein compositions. The invention also relates to methods of purifying proteins from one or more impurities.

43 Claims, 23 Drawing Sheets

(56) References Cited

FOREIGN PATENT DOCUMENTS

| JP | 2013/528183 | A | 7/2013 |
|---|---|---|---|
| JP | 2013/194054 | A | 9/2013 |
| JP | 2013/544763 | A | 12/2013 |
| JP | 2014/514345 | A | 6/2014 |
| JP | 2016/504040 | A | 2/2016 |
| WO | WO 1996/37515 | | 11/1996 |
| WO | WO-2006/031560 | A2 | 3/2006 |
| WO | 2006/073417 | A2 | 7/2006 |
| WO | 2007/011941 | A2 | 1/2007 |
| WO | 2007/087384 | A2 | 8/2007 |
| WO | 2008/119567 | A2 | 10/2008 |
| WO | 2009/026303 | A1 | 2/2009 |
| WO | WO 2009/073569 | | 6/2009 |
| WO | 2010/075238 | A1 | 7/2010 |
| WO | WO 2011/150284 | | 12/2011 |
| WO | WO 2012/037534 | | 3/2012 |
| WO | WO 2012/151199 | | 11/2012 |
| WO | WO 2014/110246 | | 7/2014 |
| WO | 2014/144632 | A2 | 9/2014 |
| WO | WO-2016009049 | A1 | 1/2016 |
| WO | 2017/134140 | A1 | 8/2017 |
| WO | WO-2018/033482 | A1 | 2/2018 |
| WO | WO-2019/038742 | | 2/2019 |

OTHER PUBLICATIONS

International Application No. PCT/US19/24683, International Preliminary Report on Patentability, mailed Oct. 22, 2020.

International Application No. PCT/US19/24683, International Search Report and Written Opinion, mailed Jul. 2, 2019.

Jones, Analysis of Polypeptides and Proteins, Adv. Drug Delivery Rev., 10(1):29-90 (1993).

Naested et al., Production of enzymatically active recombinant full-length barley high pl alpha-glucosidase of glycoside family 31 by high cell-density fermentation of Pichia pastoris and affinity purification, Protein Expr. Purif., 46(1):56-63 (2006).

Sisti et al., Preparation of lyophilized and liquid intravenous immunoglobulin G: Development and scale-up, Vox Sang, 80(4):216-224 (2001).

Yang et al., Multi-criteria manufacturability indices for ranking high-concentration monoclonal antibody formulations : Multi-criteria manufacturability indices, Biotechnol. Bioeng., 114(9):2043-2056 (2017).

Zbacnik et al., Role of Buffers in Protein Formulations, Journal of Pharmaceutical Sciences, 106(3):713-733 (2017).

Teeters, et al., "Predicting Diafiltration Solution Compositions for Final Ultrafiltration/Diafiltration Steps of Monoclonal Antibodies", Biotechnology and Bioengineering, vol. 108, No. 6, pp. 1338-1346 (2011).

* cited by examiner

Figure 21

≤ 25 μm particles, filtered (ECD >=5.0 and AR <0.7)

METHODS FOR MAKING STABLE PROTEIN COMPOSITIONS

CROSS-REFERENCE TO RELATED APPLICATIONS

This application claims the benefit of U.S. Provisional Application No. 62/656,687, filed on Apr. 12, 2018, which is hereby incorporated by reference.

FIELD OF THE INVENTION

The present application relates to methods for making stable protein compositions. The present application also relates to methods for purifying proteins of interest using purification procedures to remove one or more impurities.

BACKGROUND OF THE INVENTION

Efficient and economic large scale purification of proteins, e.g., therapeutic proteins including antibodies, is an increasingly important consideration for the biotechnology and pharmaceutical industries. As proteins are typically produced using cell culture methods, e.g., using either mammalian or bacterial host cells engineered to produce proteins of interest in appropriate media, processes for purifying proteins include many different steps to remove impurities from the media components and host cells. Although processes for purifying proteins may vary depending on the properties of a particular protein of interest under purification, the processes typically include at least steps of recovering the protein from host cells and/or cell debris, e.g., using centrifugation and/or filtration methods, and steps for purifying the proteins, e.g., using one or more chromatography and/or filtration methods, to separate the protein from various impurities.

Generally, protein purification processes include a final ultrafiltration and diafiltration (UF DF) operation. Many proteins experience stability issues during and post UF DF operations. For example, protein aggregation is a common problem following UF DF operations. Aggregation is of particular concern if proteins under purification are unstable. As a result, protein aggregates (e.g., high molecular weight (HMW) aggregates) are present or may increase in amount in protein compositions when measured post UF DF operation. However, the presence of aggregates in protein compositions post UF DF is undesirable as the aggregates may negatively impact the stability and potency of the purified protein. There is a need for methods for decreasing protein aggregation during and post UF DF operation and making stable protein compositions.

SUMMARY OF THE INVENTION

Provided herein are methods for making stable protein compositions. The present application is directed to the surprising findings that post UF DF stable protein compositions (e.g., protein compositions with reduced aggregates) can be obtained if conditions for reducing instability are present before the UF DF operation. In particular, the present application is directed to the surprising findings that adjusting the pH of a protein preparation obtained from a purification process to a target pH before a final UF DF operation results in a stable composition comprising the protein after the UF DF operation. Protein compositions prepared by the methods disclosed herein have increased stability compared to protein compositions prepared by a similar method without the pH adjusting step.

In one embodiment, disclosed herein is a method for preparing a composition comprising a protein, the method comprises providing a preparation comprising a protein of interest, the preparation is obtained after subjecting a sample comprising the protein and one or more impurities to a purification process, adjusting the pH of the preparation to a target pH prior to a final ultrafiltration and diafiltration operation, and obtaining a composition comprising the protein from the final ultrafiltration and diafiltration operation, wherein the target pH is at or about the pH of the composition comprising the protein obtained from the final ultrafiltration and diafiltration operation. In one embodiment, the pH is adjusted using a pH adjusting agent. In one embodiment, the pH adjusting agent is an acid, a base, or a buffer. In one embodiment, the target pH is from pH 4.0 to about pH 7.0 or from pH 4.0 to about pH 6.0.

In one embodiment, the acid used for adjusting the pH of the preparation is acetic acid, adipic acid, alginic acid, ascorbic acid, aspartic acid, benzene sulfonic acid, citric acid, caprylic acid, formic acid, glutamic acid, hydrochloride acid, hydrobromic acid, hydroxy acids, hyaluronic acid, lactic acid, malic acid, methanesulfonic acid, nitric acid, phosphoric acid, propionic acid, sulfuric acid, or tartaric acid. In another embodiment, the base used for adjusting the pH of the preparation is ammonia solution, ammonium carbonate, diethanolamine, calcium hydroxide, ethanolamine, lysine, poly-lysine, meglumine, potassium hydroxide, sodium bicarbonate, sodium borate, sodium carbonate, sodium hydroxide, or triethanolamine. In one embodiment, the buffer used for adjusting the pH of the preparation is acetate buffer, aspartate buffer, ascorbate buffer, citrate buffer, phosphate buffer, succinate buffer, glycine buffer, carbonate buffer, lactate buffer, Tris buffer, Bis-tris buffer, histidine buffer, HEPES buffer, MOPS buffer, MES buffer, ADA buffer, borate buffer, tartrate buffer, or benzoate buffer.

In one embodiment, the method further comprises concentrating the protein in the preparation to a target concentration. In one embodiment, the concentrating step is carried out after the pH adjusting step and before the final UF DF operation. In another embodiment, the concentrating step is carried out before the pH adjusting step. In one embodiment, the target concentration is from about 1 mg/mL to about 50 mg/mL, in another embodiment, the target concentration is from about 1 mg/mL to about 200 mg/mL, in another embodiment, the target concentration is from about 1 mg/mL to about 250 mg/mL, in another embodiment, the target concentration is from about 50 mg/mL to about 200 mg/mL, in another embodiment, the target concentration is from about 50 mg/mL to about 250 mg/mL.

In one embodiment, the final ultrafiltration and diafiltration operation is carried out using a medium that comprises a buffer, in one embodiment, the final ultrafiltration and diafiltration operation is carried out using a medium that comprises a buffer at a concentration of from 2 mM to 10 mM, from 2 mM to 50 mM, or from 2 mM to 300 mM. In another embodiment, the final ultrafiltration and diafiltration operation is carried out using a medium that comprises essentially no buffer.

In one embodiment, the composition obtained from the final ultrafiltration and diafiltration operation comprises essentially no buffer and comprises the protein at a concentration of from about 40 mg/mL to about 200 mg/mL. In one embodiment, the composition obtained from the final ultrafiltration and diafiltration operation comprises a buffer and the protein at a concentration of from about 1 mg/mL to about 200 mg/mL. In one embodiment, the composition obtained from the final ultrafiltration and diafiltration operation comprises a buffer at a concentration of from 2 mM to about 10 mM and comprises the protein at a concentration of from about 1 mg/mL to about 50 mg/mL. In one embodiment, the composition obtained from the final ultrafiltration and diafiltration operation comprises a buffer at a pH outside the buffer capacity range of the bugger and comprises the protein at a concentration of from about 1 mg/mL to about 50 mg/mL. In one embodiment, the composition obtained from the final ultrafiltration and diafiltration operation is a pharmaceutical formulation comprising the protein. In one embodiment, the composition obtained from the final ultrafiltration and diafiltration operation is a drug substance comprising the protein. In one embodiment, the composition obtained from the final ultrafiltration and diafiltration operation is more stable compared to a composition prepared by the same method without the pH adjusting step.

In one embodiment, the ultrafiltration and diafiltration operation is carried out at a temperature of from about 25° C. to about 50° C.

In one embodiment, the protein is obtained from a purification process comprises one or more steps selected from centrifugation, microfiltration, TFF, virus inactivation, affinity chromatography, cation exchange chromatography, anion exchange chromatography, hydrophobic interaction chromatography, ultrafiltration, diafiltration, SPTFF, depth filtration, and mixed-mode chromatography. In one embodiment, the purification process comprises a virus filtration step and one or more steps selected from centrifugation, microfiltration, TFF, virus inactivation, affinity chromatography, cation exchange chromatography, anion exchange chromatography, hydrophobic interaction chromatography, mixed-mode chromatography, ultrafiltration, diafiltration, SPTFF, and depth filtration, and the preparation is obtained from the virus filtration step.

In one embodiment, the purification process comprises a cation exchange chromatography step, and one or more of the following steps: centrifugation, microfiltration, TFF, virus inactivation, affinity chromatography, anion exchange chromatography, hydrophobic interaction chromatography, mixed-mode chromatography, ultrafiltration, diafiltration, SPTFF, virus filtration, and depth filtration, and the preparation is obtained from the cation exchange chromatography step. In one embodiment, the purification process comprises an anion exchange chromatography step, and one or more of the following steps: centrifugation, microfiltration, TFF, virus inactivation, affinity chromatography, cation exchange chromatography, hydrophobic interaction chromatography, mixed-mode chromatography, ultrafiltration, diafiltration, SPTFF, virus filtration, and depth filtration, and the preparation is obtained from the anion exchange chromatography step. In one embodiment, the purification process comprises hydrophobic interaction chromatography step, and one or more of the following steps: centrifugation, microfiltration, TFF, virus inactivation, affinity chromatography, cation exchange chromatography, anion exchange chromatography, mixed-mode chromatography, ultrafiltration, diafiltration, SPTFF, virus filtration, and depth filtration, and the preparation is obtained from the hydrophobic interaction chromatography step. In one embodiment, the purification process comprises a mixed-mode chromatography step, and one or more of the following steps: centrifugation, microfiltration, TFF, virus inactivation, affinity chromatography, cation exchange chromatography, anion exchange chromatography, hydrophobic interaction chromatography, ultrafiltration, diafiltration, SPTFF, virus filtration, and depth filtration, and the preparation is obtained from the mixed-mode chromatography step.

In one embodiment, the method disclosed herein further comprises adding a stabilizer to the preparation. In one embodiment, the stabilizer is one or more selected from an amino acid, a sugar, a polyol, an anti-oxidant, a chelating agent, a lipid or a lipid derivative, a salt, a polymer, an inert protein, a surfactant, and a water-miscible co-solvent.

In one embodiment, the protein that can be used in the method disclosed herein is a therapeutic protein. In one embodiment, the protein is any one of the following proteins: etanercept, aflibercept, adalimumab, epoetin alfa, darbepoetin alfa, filgrastim, pegfilgrastim, bevacizumab, cetuximab, infliximab, rituximab, eculizumab, trastuzumab, evolocumab, denosumab, romosozumab, erenumab, blinatumomab, anti-CD33 and anti-CD3 BiTE, anti-EGFRvIII and anti-CD3 BiTE, anti-DLL3 and anti-CD3 BiTE, and anti-BCMA and anti-CD3 BiTE.

BRIEF DESCRIPTION OF THE DRAWINGS

FIG. 21 shows the count of 25 μM sub-visible particles in the adalimumab formulations measured by MFI in Example 7.

DETAILED DESCRIPTION OF THE INVENTION

Figure 1:
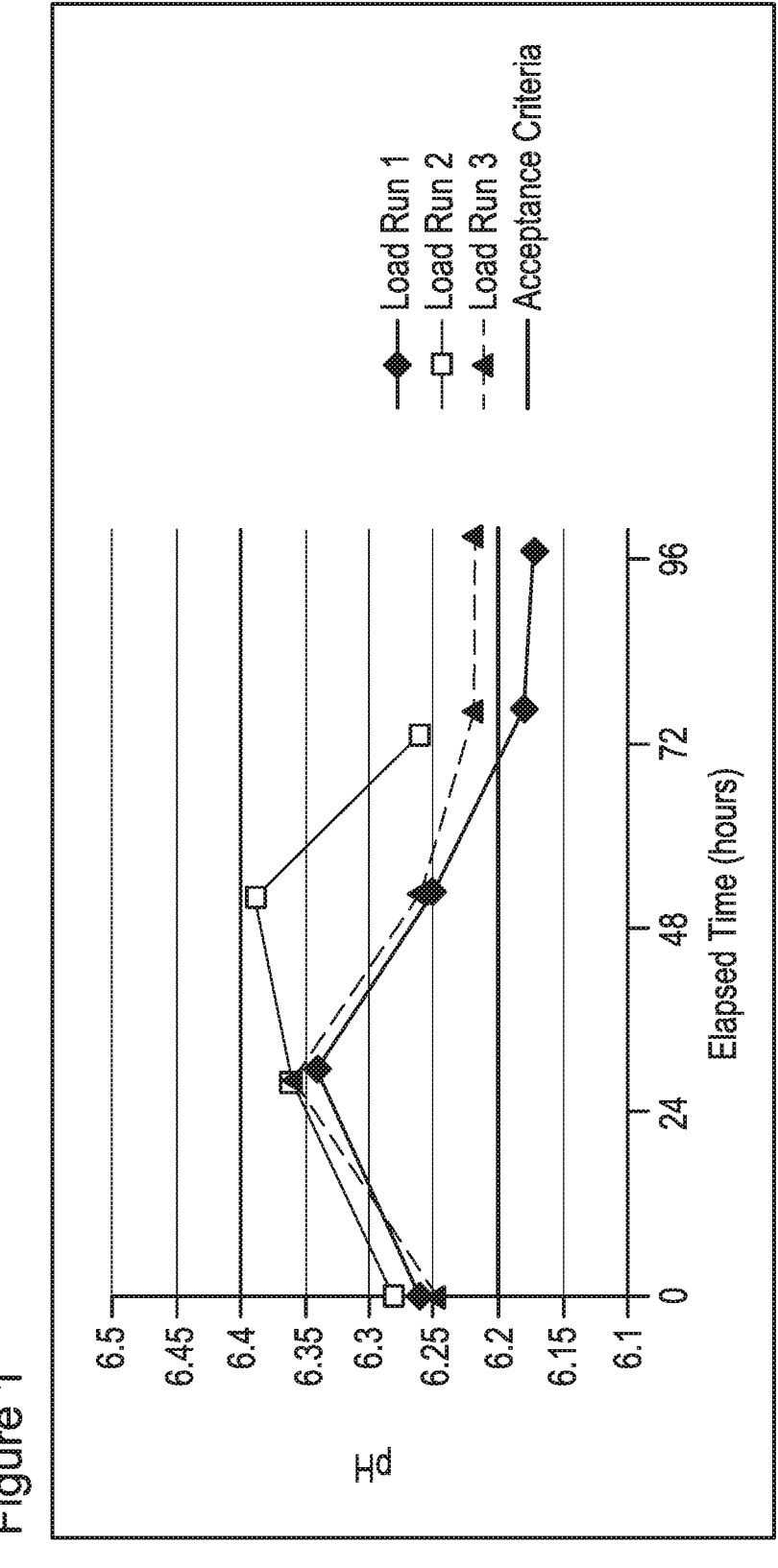
FIG. 1 shows the pH stability of the conditioned AEX intermediate pool at controlled room temperature (CRT) in the assay of Example 1.

Disclosed herein are methods for making stable protein compositions. A "stable" protein composition is one in which the protein therein essentially retains its physical stability and/or chemical stability and/or biological activity upon storage. Stability of protein compositions can be determined by the presence and/or percentage of aggregated proteins such as high molecular weight (HMW) aggregates in the composition, or by the presence and/or percentage of protein degradation, e.g., degradation due to oxidation and/or deamidation, or by shift in pH of the composition upon storage. For example, a stable protein composition may include no more than 7%, or no more than 5%, or no more than 2%, or no more than 1.2%, or no more than 1%, or no more than 0.8%, or no more than 0.5% protein aggregates, or a stable protein composition may contain no detectable degraded protein products by, e.g., oxidization and/or deamidation, or a stable protein composition may show a maximum shift in pH of no more than 0.1 pH units or no more than 0.2 pH units upon storage.

Various analytical techniques for measuring protein stability are known and available in the art. For example, size exclusion chromatography is a technique widely used for evaluating protein aggregates. See e.g., Theory and Practice of Size Exclusion Chromatography for the Analysis of Protein Aggregates, Fekete S. et al., Journal of Pharmaceutical and Biomedical Analysis, 101:161-173 (2014). Methods for analyzing protein stability and aggregates are also reviewed in e.g., Peptide and Protein Drug Delivery, 247-301, Vincent Lee Ed Marcel Dekker, Inc., New York, N.Y., Pubs. (1991) and Analysis of Polypeptides and Proteins, Jones, A. Adv. Drug Delivery Rev. 10: 29-90 (1993).

In one embodiment, the method disclosed herein comprises providing a preparation comprising a protein of interest, the preparation is obtained after subjecting a sample comprising the protein and one or more impurities to a purification process, adjusting the pH of the preparation to a target pH prior to a final ultrafiltration and diafiltration operation, and obtaining a composition comprising the protein from the final ultrafiltration and diafiltration operation, wherein the target pH is at or about the pH of the composition comprising the protein obtained from the final ultrafiltration and diafiltration operation.

Target pH and pH Adjusting Agents

The target pH represents a pH range or a pH value at which a protein of interest is stable. In some embodiments, the target pH is in the range of from about 3 to about 10, from about 4.0 to about 5.0, from about 4.0 to about 6.0, from about 4.0 to about 7.0, from about 5.0 to about 6.0, from about 6.0 to about 7.0, from about 4.2 to about 5.2, from about 4.4 to about 5.4, from about 4.6 to about 5.6, from about 4.8 to about 5.8, from about 5.2 to about 6.2, from about 5.4 to about 6.4, from about 5.6 to about 6.6, from about 5.8 to about 6.8, from about 4.9 to about 5.6, from about 5.0 to about 5.5, from about 5.1 to about 5.4, from about 5.1 to about 5.3, from about 5.1 to about 5.2, from about 5.2 to about 5.3, from about 6.1 to about 6.5, or from about 6.1 to about 6.3. In some embodiments, the target pH is about 4.0, about 4.2, about 4.4, about 4.6, about 4.8, about 5.0, about 5.2, about 5.4, about 5.6, about 5.8, about 6.0, about 6.2, about 6.4, about 6.6, about 6.8, or about 7.0.

As used herein, the term "about," when used to modify a particular value or range, is understood to mean that there can be variations in a given value or range, including within 20 percent, e.g., within 10 percent, 5 percent, 4 percent, 3 percent, 2 percent, or 1 percent of the stated value or range.

In one embodiment of the methods disclosed herein, the pH adjusting step is carried out using a pH adjusting agent. In one embodiment, the pH adjusting agent is an acid, in one embodiment, the pH adjusting agent is a base, in one embodiment, the pH adjusting agent is a buffer.

In one embodiment, the pH adjusting agent is an acid. An acid may be used for adjusting the pH of the preparation if the target pH is lower (or more acidic) than the pH of the preparation. Typically, acids that are nontoxic and do not adversely affect the protein (e.g., adversely affect the stability of the protein) may be used as pH adjusting agents. In one embodiment, the acid is an inorganic acid, in another embodiment, the acid is an organic acid. Nonlimiting examples of acids that may be used for adjusting the pH of the preparation include acetic acid, adipic acid, alginic acid, ascorbic acid, aspartic acid, benzene sulfonic acid, benzoic acid, boric acid, camphorsulfonic acid, citric acid, caprylic acid, formic acid, glutamic acid, hydrochloride acid, hydrobromic acid, hydroxy acids (including alpha, beta and omega hydroxy acids), hyaluronic acid, lactic acid, malic acid, methanesulfonic acid, nitric acid, phosphoric acid, propionic acid, sulfuric acid, sulfonic acid, transexamic acid, and tartaric acid. In some embodiments, the acid is acetic acid, ascorbic acid, aspartic acid, glutamic acid, hydrochloride acid, hydrobromic acid, lactic acid, sulfuric acid, propionic acid, tartaric acid, hydroxy acids (including alpha, beta and omega hydroxy acids), or hyaluronic acid. In some preferred embodiments, the acid is lactic acid, hydroxy acids (including alpha, beta and omega hydroxy acids), or hyaluronic acid.

In one embodiment, the pH adjusting agent is a base. A base may be used for adjusting the pH of the preparation if the target pH is higher (or more basic) than the pH of the preparation. Typically, bases that are nontoxic and do not adversely affect the protein (e.g., adversely affect the stability of the protein) may be used as pH adjusting agents. In one embodiment, the base is an inorganic base, in another embodiment, the base is an organic base. Nonlimiting examples of bases that may be used for adjusting the pH of the preparation include ammonia solution, ammonium carbonate, diethanolamine, calcium hydroxide, ethanolamine, lysine, meglumine, poly-lysine, potassium hydroxide, sodium bicarbonate, sodium borate, sodium carbonate, sodium hydroxide, and triethanolamine. In one embodiment, the base is potassium hydroxide or sodium hydroxide.

In one embodiment, the pH adjusting agent is a buffer. Buffers may be added to the preparation to adjust and stabilize the pH of the preparation to a target pH. A buffer typically comprises two chemical species that are related by a change in protonation state, e.g., an acid and its conjugate base or a base and its corresponding conjugate acid. Buffer or buffering capacity is a property of buffer and measures how well a buffer maintains pH. Factors that affect buffer capacity of a buffer include the concentration of the buffer, typically, the higher the concentration, the higher the buffer capacity. In addition, buffers generally exhibit a buffer capacity range that is approximately ±1 (one) pH unit around the pKa of the corresponding acid form. For example, the pKa of acetic acid is ~4.8, and an acetate buffer has a buffer capacity at a pH range of approximately about pH 3.8 to about pH 5.8.

Generally, buffers that are nontoxic and do not adversely affect the stability of the protein (e.g., adversely affect the stability of the protein) may be used as pH adjusting agents. Buffers useful for adjusting and/or maintaining pH of protein preparations are well known in the art, e.g., A Guide for the Preparation and Use of Buffers in Biological Systems, Gueffroy, D., ed. Calbiochem Corporation (1975); Zbacnik T. J. et al., Role of Buffers in Protein Formulations, Journal of Pharmaceutical Sciences 106:713-733 (2017). Nonlimiting examples of buffers that may be used for adjusting the pH of the preparation include acetate buffer, aspartate buffer, ascorbate buffer, borate buffer, benzoate buffer, carbonate buffer, citrate buffer, glycine buffer, HEPES buffer, MOPS buffer, MES buffer, N-(2-acetamido)iminodiacetic acid (ADA) buffer, histidine buffer, lactate buffer, phosphate buffer, succinate buffer, Tris buffer, Bis-tris buffer, and tartrate buffer.

In some embodiments, the pH adjusting agent is a buffer with low buffer capacity. This may be achieved by, e.g., using a buffer at a pH within the buffer capacity range of the buffer but at a low concentration, or using a buffer at a pH that is outside the buffer capacity range of the buffer (e.g., at a pH that is greater than one pH unit of the pKa of the corresponding acid form of the buffer). In some embodiments, the pH adjusting agent is a buffer at a concentration of from 2 mM to 20 mM and at a pH within the buffer capacity range of the buffer. In some embodiments, the pH adjusting agent is a buffer at a concentration of from 2 mM to 10 mM and a pH within the buffer capacity range of the buffer. In some embodiments, the pH adjusting agent is a buffer at a pH outside the buffer capacity range of the buffer. In some embodiments, the pH adjusting agent is a buffer at a pH outside the buffer capacity range of the buffer and a concentration of from 2 mM to 50 mM. A person of ordinary skill in the art can determine buffer concentration or concentration range of a particular buffer that provides low buffer capacity. Likewise, a person of ordinary skill in the art can determine buffer capacity range of a given buffer and the proper amount of the buffer to use outside the range that provides low buffer capacity.

Concentrating Step

In some embodiments, the method disclosed herein further comprises concentrating the protein in the preparation to a target concentration. In one embodiment, the concentrating step is carried out before the final UF DF operation. In one embodiment, the concentrating step is carried out before the pH adjusting step. In one embodiment, the concentrating step is carried out after the pH adjusting step and before the final UF DP operation. In one embodiment, the concentrating step is carried out after the final UF DF operation. In one embodiment, the method disclosed herein further comprises first concentrating the protein in the preparation to an intermediate concentration before the final UF DF operation and further concentrating the protein to a target concentration after the final UF DF operation. The target concentration is at or near the concentration of the protein in the composition obtained from the final UF DF operation.

Proteins may be concentrated using methods known in the art. Nonlimiting exemplary methods that may be used for concentrating proteins include ultrafiltration, concentration using membrane concentrators (e.g., cellulose membrane concentrators) with a centrifugal force, dialysis against a water absorbing material (e.g., a water absorbing polymer), salting out (e.g., using ammonium sulfate), and chromatography methods (e.g., size exclusion chromatography).

In some embodiment, the target concentration of the concentrating step is at or about the concentration of the protein in the composition obtained from the final UF DF operation. In some embodiments, the target concentration of the concentrating step is in the range of from about 1 mg/mL to about 250 mg/mL, from about 1 mg/mL to about 200 mg/mL, from about 1 mg/mL to about 50 mg/mL, from about 10 mg/mL to about 250 mg/mL, from about 10 mg/mL to about 200 mg/mL, from about 20 mg/mL to about 200 mg/mL, from about 30 mg/mL to about 200 mg/mL, from about 40 mg/mL to about 200 mg/mL, from about 50 mg/mL to about 200 mg/mL, from about 60 mg/mL to about 200 mg/mL, from about 70 mg/mL to about 200 mg/mL, from about 80 mg/mL to about 200 mg/mL, from about 90 mg/mL to about 200 mg/mL, from about 100 mg/mL to about 200 mg/mL, from about 110 mg/mL to about 200 mg/mL, from about 120 mg/mL to about 200 mg/mL, from about 130 mg/mL to about 200 mg/mL, from about 140 mg/mL to about 200 mg/mL, from about 150 mg/mL to about 200 mg/mL, from about 160 mg/mL to about 200 mg/mL, from about 170 mg/mL to about 200 mg/mL, from about 180 mg/mL to about 200 mg/mL, or from about 190 mg/mL to about 200 mg/mL. In some embodiments, the target concentration of the concentrating step is about 10 mg/mL, about 20 mg/mL, about 30 mg/mL, about 40 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL.

Processes for Protein Purification

In some embodiments of the methods disclosed herein, the preparation of which the pH is adjusted is obtained by subjecting a sample comprising the protein of interest and one or more impurities to a purification process. Processes for purifying a protein of interest encompasses all process steps from cell harvest to the final purified protein and typically include at least steps of recovering the protein from host cells and/or cell debris, e.g., using centrifugation and/or filtration methods, and steps for purifying the proteins, e.g., using one or more chromatography and/or filtration methods, to separate the protein from various impurities. Purification steps typically used in the art are described below.

In some embodiments, a protein of interest is produced in recombinant systems, e.g., using host cells. In recombinant systems, proteins may be secreted from host cells into growth media or may be made intracellularly. Purification processes start from recovering a protein of interest from host cells or cell media. In some embodiments, the purification process comprises one or more steps of: centrifugation, microfiltration, single-pass tangential-flow filtration (SPTFF), ultrafiltration and diafiltration to recover the protein of interest from host cells. For example, if the protein is produced intracellularly, as a first step, the host cells are lysed, e.g., by mechanical homogenization, osmatic shock or enzymatic treatment, to release the protein. The debris are removed by, e.g., centrifugation, microfiltration, ultrafiltration and/or diafiltration. Where the protein is secreted into the medium, supernatants from such expression systems can be first concentrated ultrafiltration and/or diafiltration using a commercially available protein concentration filter, e.g., an Amicon™ or Millipore Pellicon™ ultrafiltration unit.

The protein recovered from host cells is then purified using various methods known and used in the art, including viral inactivation steps, various chromatography methods, and various filtration methods.

In some embodiment, the purification process comprises a virus inactivation step, e.g., by using virus inactivating agents and/or methods that render viruses inactive, or unable to replicate or infect. Many, virus inactivating agents are known and used in the art. See, e.g., Gail Sofer, "Virus Inactivation in the 1990s—and into the 21$^{st}$ Century, Part 4, Culture Media. Biotechnology Products, and Vaccines," Biopharm International, pp. 50-57 (2003). Exemplary virus inactivation methods include solvent/detergent inactivation (e.g. with Triton X 100): pasteurization (heating); acidic pH inactivation (e.g., at pH 3-5); and ultraviolet (UV) inactivation. It is also possible to combine two or more of these methods, e.g., perform acidic pH inactivation at elevated temperature, to inactivate viruses.

In certain embodiments, the purification process comprises affinity chromatography steps. Affinity chromatography refers to a protein separation technique in which a protein of interest (e.g., an Fc region containing; protein of interest or antibody) is specifically bound to a ligand that is specific for the target protein. In certain embodiments, the purification process comprises the use of a Protein A based affinity resin for use in the affinity chromatography steps. The Protein A can be native Protein A (from Staph. Aureus), recombinant Protein A or functional variant thereof. Examples of Protein A resins that may be used include: ProSep-vA HC, ProSep Ultra Plus, MabSelect, MabSelect SuRe and other commercially available affinity resins. Other affinity ligands/resins could be utilized in the purification methods described herein, such as, for example, Protein C and other Fe binding proteins (e.g., single chain camelid antibodies). The protein of interest generally retains its specific binding affinity for the ligand during the chromatographic steps, while other impurities in the mixture do not bind appreciably or specifically to the ligand. The protein of interest is then eluted from the affinity chromatography column using solutions known in the art, e.g., solutions recommended by the manufacture of the affinity resin used in the affinity chromatography step.

In certain embodiments, the purification process comprises ion exchange chromatography steps. Ion exchange chromatography can be membrane ion exchange chromatography or column ion exchange chromatography. Ion exchange chromatography separates proteins based on the difference in their respective ionic charges, and include cationic exchange chromatography and anionic exchange chromatography. The use of a cationic exchange chromatography versus an anionic exchange chromatography is based on the overall charge of the protein. It is within the skill of a person of ordinary skill in the art to determine whether to use only cation exchange chromatography, only anion exchange chromatography, or a combination of the two to purify a protein of interest. In some embodiments, the purification process employs only a cation exchange step. In some embodiments, the purification process employs only an anion exchange step. In some embodiments, the purification process employs an anionic exchange step prior to the use of a cationic exchange step. In certain embodiments, the purification process employs a cationic exchange step prior to the use of an anionic exchange step.

In ion exchange chromatography, the protein of interest in the preparation is attracted by opposite charges attached to a chromatography matrix, provided the ionic strength of the surrounding solution or buffer is low. Elution is generally achieved by increasing the ionic strength (i.e., conductivity) of the elution solution to compete with the solute for the charged sites of the ion exchange matrix. The conductivity of a preparation can be increased, for example, by the addition of salt to the preparation. The salt which may be used will depend on the pH of the preparation and can be readily identified by one of ordinary skill in the art. In some embodiments, the amount of salt added ranges from 25 mM to 500 mM and from 100 mM to 250 mM Changing the pH and thereby altering the charge of the protein of interest is another way to achieve elution of the protein. The change in conductivity or pH may be gradual (gradient elution) or stepwise (step elution).

Cation exchange materials or resins are available from commercial sources. Nonlimiting cationic materials suitable for cation exchange chromatography include carboxymethyl (CM), sulfoethyl (SE), sulfopropyl (SP), phosphate (P), sulfonate (S) and Fractogel® EMD cation exchange materials from Millipore Cellulose ion exchange resins such as DE23™, DE32™, DE52™, CM-23™, CM-32™, and CM-52™ are available from Whatman Ltd Maidstone, Kent, U.K. SEPHADEX®-based and cross-linked ion exchangers are also known. For example, DEAE-, QAE-, CM-, and SP-SEPHADEX® and DEAE-, Q-, CM- and S-SEPHAROSE® and SFPHAROSE® Fast Flow are all available from Pharmacia AB. Further, both DEAF and CM derivatized ethylene glycol-methacrylate copolymer such as TOYOPEARL™ DEAE-650S or M and TOYOPEARL™ CM-650S or M are available from Toso Haas Co., Philadelphia, Pa. Fractogel® EMD cation exchange materials include Fractogel® EMD SO3-(S), Fractogel® EMD COO-(S), Fractogel® EMD SO3-(M), Fractogel® EMD SE Hicap (M), and Fractogel® EMD COO-(M).

Anion exchange materials or resins are available from commercial sources. Non-limiting examples of anionic exchange substituents include diethylaminoethyl (DEAE), quaternary aminoethyl(QAE) and quaternary amine (Q) groups. Exemplary anion exchange materials include Fractogel® EMD TMAE (S), Fractogel® EMD DEAE (S), Fractogel® EMD DMAE (S), Fractogel® EMD TMAE (M), Fractogel® EMD TMAE Hicap (M), Fractogel® EMD DEAE (M), Fractogel® EMD DMAE (M) available from Millipore.

In some embodiments, the purification process comprises hydrophobic interaction chromatography (HIC) steps Generally, HIC is useful for removing protein aggregates, such as antibody aggregates, and process-related impurities. In some embodiments, HIC is performed following salt precipitations or ion exchange procedures as hydrophobic interactions are strongest at high ionic strength Many HIC columns are available commercially Nonlimiting examples include. Phenyl Sepharose™ 6 Fast Flow column with low or high substitution (Pharmacia LKB Biotechnology. AB, Sweden); Phenyl Sepharose™ High Performance column (Pharmacia LKB Biotechnology, AB, Sweden); Octyl Sepharose™ High Performance column (Pharmacia LKB Biotechnology, AB, Sweden); Fractogel™ EMD Propyl or Fractogel™ EMD Phenyl columns (E. Merck, Germany): Macro-Prep™ Methyl or Macro-Prep™ t-Butyl Supports (Bio-Rad, California); WP HI-Propyl (C3)™ column (J. T. Baker, New Jersey); Phenyl Sepharose HiSub FF (GE Healthcare), and Toyopearl™ ether, phenyl or butyl columns (TosoHaas, Pa.)

In some embodiments, the purification process comprises mixed-mode or multimode chromatography (MMC) MMC is a chromatographic method in which solutes interact with stationary phase through more than one interaction mode or mechanism. MMC using multimodal functional ligands can adsorb a protein of interest with the combination of ionic interactions, hydrogen bonds and hydrophobic interactions. Mixed-mode resins can directly capture target proteins at relatively high salt concentration without dilution or other additives due to their multiple binding interactions. Non-limiting exemplary commercially available mixed-mode resins include Capto MMC, Capto adhere and Capto Core 700 from GE Healthcare, PPA Hypercel, HEA Hypercel and MEP Hypercel from Pall Corporation, Eshmuno HCX from Merck Millipore, Toyopearl MX-Trp-650 M from TOSOH Bioscience, and Nuvia cPrime, CHT Ceramic Hydroxyapatite, and CFT Ceramic Fluoroapatite from Bio-Rad.

In some embodiments, the protein purification process comprises ultrafiltration and/or diafiltration steps. Ultrafiltration is a separation process through a semipermeable membrane that retains macromolecules while allowing solvent and small solute molecules to pass through. Ultrafiltration process is known in the art and commonly used in protein purification processes, e.g., Zeman et al., Microfiltration and Ultrafiltration: Principles and Applications, Marcel Dekker, Inc., pp. 299-301 (1996). Ultrafiltration may be used to purifying and concentrating micro-molecules such as proteins. Diafiltration is a method that uses ultrafiltration membranes to remove, replace, or lower the concentration of salts or solvents from solutions containing proteins, peptides, nucleic acids, and other biomolecules. In certain embodiments, the protein purification process employs ultrafiltration and/or diafiltration operations when recovering a protein of interest from host cells. In other embodiments, ultrafiltration and/or diafiltration is employed in other steps of the purification process, including as the penultimate or the final step of purification. Ultrafiltration and diafiltration steps may be used for concentrating proteins, or buffer change, or formulating a protein of interest into a desired solution or a desired buffer.

In some embodiments, the protein purification process comprises a virus filtration step between and after any of the steps described above, as appropriate. In certain embodiments, the purification process comprises a virus filtration step after viral inaction, or after affinity chromatography, or after cation exchange chromatography, or after anion exchange chromatography, or after HIS, or after mixed-mode chromatography. In certain embodiments, the purification process comprises a virus filtration step before cation exchange chromatography, or before anion exchange chromatography, or before HIC, or before mixed-mode chromatography. In certain embodiments, the purification process comprises a virus filtration step as the final step of the purification, or the penultimate of purification, e.g., before the final ultrafiltration and diafiltration operation.

Virus filtration may be achieved by the use of appropriate filters, Non-limiting examples of suitable filters for virus filtration include Ultipor DV50™ filter from Pall Corporation, Viresolve™ filters Billerica, Mass.); Zeta Plus VR™ filters (CUNO; Meriden, Conn.); and Planova™ filters (Asahi Kasei Pharma, Planova Division, Buffalo Grove, Ill.). In some embodiments, the virus filtration step employs a prefilter, which can be of any format, including but not limited to, a membrane, depth filter, chromatography column or combinations thereof. Non-limiting examples of depth filters that can be used for virus filtration include the Cuno™ mod& 30/60ZA depth filters (3M Corp.), and 0.45/0.2 μm Sartopore™ bi-layer filter cartridges.

In certain embodiments, the purification process can include additional process steps including formulation and/or concentration steps. In one embodiment, the purification process further comprises sterile filtration and/or absolute filtration. Sterile filtration is typically carried out using Normal Flow Filtration (NFF) where the direction of the fluid stream is perpendicular to the filter medium (e.g., a membrane) coder an applied pressure.

In some embodiments of the methods disclosed herein, the preparation of which the pH is adjusted is obtained from a purification process that comprises one or more of the following steps: centrifugation, microfiltration, Tangential Flow Filtration (TFF), virus inactivation, affinity chromatography, cation exchange chromatography, anion exchange chromatography, hydrophobic interaction chromatography, mixed-mode chromatography, ultrafiltration, diafiltration, single pass tangential flow filtration (SPTFF), depth filtration, and virus filtration.

In some embodiments, the preparation of which the pH is adjusted is obtained from a purification process that comprises a virus filtration step and one or more of the following steps: centrifugation, microfiltration, Tangential Flow Filtration (TFF), virus inactivation, affinity chromatography, cation exchange chromatography, anion exchange chromatography, hydrophobic interaction chromatography, mixed-mode chromatography, ultrafiltration, diafiltration, single pass tangential flow filtration (SPTFF), and depth filtration, and wherein the preparation is obtained from the virus filtration step. In some embodiments, the virus filtration step is the penultimate step of the purification process and the preparation is obtained from the virus filtration step. In some embodiments, the virus filtration step is the final step of the purification process and the preparation is obtained from the virus filtration step.

In some embodiments, the preparation of which the pH is adjusted is obtained from a purification process that comprises a cation exchange chromatography step and one or more of the following steps: centrifugation, microfiltration, Tangential Flow Filtration (TFF), virus inactivation, affinity chromatography, anion exchange chromatography, hydrophobic interaction chromatography, mixed-mode chromatography, ultrafiltration, diafiltration, single pass tangential flow filtration (SPTFF), depth filtration, and virus filtration, and wherein the preparation is obtained from the cation exchange chromatography step. In some embodiments, the cation exchange chromatography step is the penultimate step or the final step of the purification process and the preparation is obtained from the cation exchange chromatography step.

In some embodiments, the preparation of which the pH is adjusted is obtained from a purification process that comprises an anion exchange chromatography step and one or more of the following steps: centrifugation, microfiltration, Tangential Flow Filtration (TFF), virus inactivation, affinity chromatography, cation exchange chromatography, hydrophobic interaction chromatography, mixed-mode chromatography, ultrafiltration, diafiltration, single pass tangential flow filtration (SPTFF), depth filtration, and virus filtration, and wherein the preparation is obtained from the anion exchange chromatography step. In some embodiments, the anion exchange chromatography step is the penultimate step or the final step of the purification process and the preparation is obtained from the anion exchange chromatography step.

In some embodiments, the preparation of which the pH is adjusted is obtained from a purification process that comprises a hydrophobic interaction chromatography step and one or more of the following steps: centrifugation, microfiltration, Tangential Flow Filtration (TFF), virus inactivation, affinity chromatography, cation exchange chromatography, anion exchange chromatography, mixed-mode chromatography, ultrafiltration, diafiltration, single pass tangential flow filtration (SPTFF), depth filtration, and virus filtration, and wherein the preparation is obtained from the hydrophobic interaction chromatography step. In some embodiments, the hydrophobic interaction chromatography step is the penultimate step or the final step of the purification process and the preparation is obtained from the hydrophobic interaction chromatography step.

In some embodiments, the preparation of which the pH is adjusted is obtained from a purification process that comprises a mixed-mode chromatography step and one or more of the following steps: centrifugation, microfiltration, Tangential Flow Filtration (TFF), virus inactivation, affinity chromatography, cation exchange chromatography, anion exchange chromatography, hydrophobic interaction chromatography, ultrafiltration, diafiltration, single pass tangential flow filtration (SPTFF), depth filtration, and virus filtration, and wherein the preparation is obtained from the mixed-mode chromatography step. In some embodiments, the mixed-mode chromatography step is the penultimate step or the final step of the purification process and the preparation is obtained from the mixed-mode chromatography step.

In some embodiments, the preparation of which the pH is adjusted is obtained from a purification process that comprises a virus filtration step and one or more of the following steps: virus inactivation, affinity chromatography, cation exchange chromatography, anion exchange chromatography, hydrophobic interaction chromatography, and mixed-mode chromatography, and wherein the preparation is obtained from the virus filtration step. In some embodiments, the virus filtration step is the penultimate step of the purification process and the preparation is obtained from the virus filtration step. In some embodiments, the virus filtration step is the final step of the purification process and the preparation is obtained from the virus filtration step.

In some embodiments, the preparation of which the pH is adjusted is obtained from a purification process that comprises a cation exchange chromatography step and one or more of the following steps: virus inactivation, affinity chromatography, anion exchange chromatography, hydrophobic interaction chromatography, mixed-mode chromatography, and virus filtration, and wherein the preparation is obtained from the cation exchange chromatography. In some embodiments, the cation exchange chromatography step is the penultimate step or the final step of the purification process and the preparation is obtained from the cation exchange chromatography step.

In some embodiments, the preparation of which the pH is adjusted is obtained from a purification process that comprises an anion exchange chromatography step and one or more of the following steps: virus inactivation, affinity chromatography, cation exchange chromatography, hydrophobic interaction chromatography, mixed-mode chromatography, and virus filtration, and wherein the preparation is obtained from the anion exchange chromatography step. In some embodiments, the anion exchange chromatography step is the penultimate step or the final step of the purification process and the preparation is obtained from the anion exchange chromatography step.

In some embodiments, the preparation of which the pH is adjusted is obtained from a purification process that comprises a hydrophobic interaction chromatography step and one or more of the following steps: virus inactivation, affinity chromatography, anion exchange chromatography, cation exchange chromatography, mixed-mode chromatography, and virus filtration, and wherein the preparation is obtained from the hydrophobic interaction chromatography step. In some embodiments, the hydrophobic interaction chromatography step is the penultimate step or the final step of the purification process and the preparation is obtained from the hydrophobic interaction chromatography step.

In some embodiments, the preparation of which the pH is adjusted is obtained from a purification process that comprises a mixed-mode chromatography step and one or more of the following steps: virus inactivation, affinity chromatography, anion exchange chromatography, hydrophobic interaction chromatography, cation exchange chromatography, and virus filtration, and wherein the preparation is obtained from the mixed-mode chromatography step. In some embodiments, the mixed-mode chromatography step is the penultimate step or the final step of the purification process and the preparation is obtained from the mixed-mode chromatography step.

Final Ultrafiltration and Diafiltration (UF DF) Operation and Compositions Obtained Therefrom in some embodiments, the methods disclosed herein comprises the step of Obtaining a composition comprising the protein from the final UF DF operation. In some embodiments, the composition obtained from the final UF DF operation is a drug substance (DS) comprising the protein. In some embodiments, the composition obtained from the final UF DF operation is a pharmaceutical formulation comprising the protein. In other words, the final UF DF operation puts the protein of interest into a composition intended for the protein. In some embodiments, the method further comprises sterile filtration and/or absolute filtration steps after the final UF DF operation. In some embodiments, the final UF DF operation is the penultimate or the final step of the purification process from which the preparation of which the pH is adjusted is Obtained.

In some embodiments, the composition obtained from the final UF DF operation comprises the protein of interest at a concentration of from about 1 mg/mL to about 50 mg/ml, from about 1 mg/mL to about 250 mg/mL, about 1 mg/mL to about 200 mg/mL, from about 10 mg/mL to about 200 mg/mL, from about 20 mg/mL to about 200 mg/mL, from about 30 mg/mL to about 200 mg/mL, from about 40 mg/mL to about 200 mg/mL, from about 50 mg/mL to about 200 mg/mL, from about 60 mg/mL to about 200 mg/mL, from about 70 mg/mL to about 200 mg/mL, from about 80 mg/mL to about 200 mg/mL, from about 90 mg/mL to about 200 mg/mL, from about 100 mg/mL to about 200 mg/mL, from about 110 mg/mL to about 200 mg/mL, from about 120 mg/mL to about 200 mg/mL, from about 130 mg/mL to about 200 mg/mL, from about 140 mg/mL to about 200 mg/mL, from about 150 mg/mL to about 200 mg/mL, from about 160 mg/mL to about 200 mg/mL, from about 170 mg/mL to about 200 mg/mL, from about 180 mg/mL to about 200 mg/mL, or from about 190 mg/mL to about 200 mg/mL. In some embodiments, the composition obtained from the final UF DF operation comprises the protein of interest at a concentration of about 10 mg/mL, about 20 mg/mL, about 30 mg/mL, about 40 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL.

In some embodiments, the composition obtained from the final UF DF operation has a pH or pH range, which is at or about the target pH of the pH adjusting step pH values for the target pH are disclosed above.

In some embodiments, the composition obtained from the final UF DF operation comprises a buffer, e.g., to maintain the pH of the composition. Any buffer disclosed above may be comprised in the composition. In some embodiments, the composition obtained from the final UF DF operation comprises a buffer at a concentration of from 2 mM to 500 mM, from 2 mM to 50 mM, or from 2 mM to 10 mM, or about 10 mM to 50 mM, or from 50 to 500 mM. In some embodiments, the composition obtained from the final UF DF operation comprises a buffer at a concentration of from about 50 mM to about 300 mM, front about 60 mM to about 300 mM, from about 70 mM to about 300 mM, from about 80 mM to about 300 mM, from about 90 mM to about 300 mM, from about 100 mM to about 300 mM, from about 120 mM to about 300 mM, from about 140 mM to about 300 mM, from about 160 mM to about 300 mM, from about 180 mM to about 300 mM, front about 200 mM to about 300 mM, from about 220 mM to about 300 mM, or from about 250 mM to about 300 mM. In some embodiments, the composition obtained from the final UF DF operation comprises a buffer at a concentration of 2 mM, about 2.5 mM, about 5 mM, about 10 mM, about 20 mM, about 30 mM, about 40 mM, about 50 mM, about 70 mM, about 90 mM, about 100 mM, about 120 mM, about 150 mM, about 170 mM, about 200 mM, about 220 mM, about 250 mM, about 270 mM, or about 300 mM. In the embodiments where the composition obtained from the final UF DF operation comprises a buffer, the protein of interest comprised in the composition can be at any of the concentrations described above.

In some embodiments, the composition obtained from the final UF DF operation comprises a buffer with low buffer capacity (e.g., buffer at a low concentration and a pH within the buffer capacity range of the buffer, or buffer at a pH that is outside the buffer capacity range of the buffer. For example, an acetate buffer at a pH that is outside its buffer capacity range of approximately about pH 3.8 to about pH 5.8 has low buffer capacity.) and comprises the protein of interest at a concentration of from about 1 mg/mL to about 50 mg/mL. In some embodiments, the composition obtained from the final UF DF operation comprises a buffer at a concentration of from 2 mM to 10 mM and a pH within the buffer capacity range of the buffer, and comprises the protein of interest at a concentration of from about 1 mg/mL to about 50 mg/mL, or from about 1 mg/mL to about 40 mg/mL, or about 10 mg/mL, or about 20 mg/mL, or about 30 mg/mL, or about 40 mg/mL, or about 50 mg/mL In some embodiments, the composition obtained from the final UF DF operation comprises a buffer at a concentration of from 2 mM to 20 mM and a pH within the buffer capacity range of the buffer, and comprises the protein of interest at a concentration of front about 1 mg/mL to about 50 mg/ml, or from about 1 mg/mL to about 40 mg/mL, or about 10 mg/mL, or about 20 mg/mL, or about 30 mg/mL, or about 40 mg/mL, or about 50 mg/mL. In some embodiments, the composition obtained from the final UF DF operation comprises a buffer at a pH that is outside the buffer capacity range of the buffer and a concentration of from 2 mM to 50 mM, and comprises the protein of interest at a concentration of from about 1 mg/mL to about 50 mg/ml, or from about 1 mg/mL to about 40 mg/mL, or about 10 mg/mL, or about 20 mg/mL, or about 30 mg/mL, or about 40 mg/mL, or about 50 mg/mL In some embodiments, the composition obtained from the final UF DF operation comprises a buffer at a pH that is outside the buffer capacity range of the buffer and a concentration of from 2 mM to 40 mM, and comprises the protein of interest at a concentration of from about 1 mg/mL to about 50 mg/ml, or from about 1 mg/mL to about 40 mg/mL, or about 10 mg/mL, or about 20 mg/mL, or about 30 mg/mL, or about 40 mg/mL, or about 50 mg/mL.

In some embodiments, the composition obtained from the final UF DF operation comprises essentially no buffer Such compositions are also referred to as buffer free compositions. The phrase "essentially no buffer" or "essentially no buffer agent" refers to that there is less than 2 mM, or less than 1 mM, or less than 0.5 mM, or less than 0.25 mM of a standard buffer Typically in such embodiments, the composition comprises the protein of interest at a concentration of from about 1 mg/mL to about 200 mg/mL. Preferably, the composition comprises the protein of interest at a concentration of from about 40 mg/mL to about 200 mg/mL, about 50 mg/mL to about 200 mg/mL, from about 60 mg/mL to about 200 mg/mL, from about 70 mg/mL to about 200 mg/mL, from about 80 mg/mL to about 200 mg/mL, from about 90 mg/mL to about 200 mg/mL, from about 100 mg/mL to about 200 mg/mL, from about 110 mg/mL to about 200 mg/mL, from about 120 mg/mL to about 200 mg/mL, from about 130 mg/mL to about 200 mg/mL, from about 140 mg/mL to about 200 mg/mL, from about 150 mg/mL to about 200 mg/mL, from about 160 mg/mL to about 200 mg/mL, from about 170 mg/mL to about 200 mg/mL, from about 180 mg/mL to about 200 mg/mL, or from about 190 mg/mL to about 200 mg/mL, or the composition comprises the protein of interest at a concentration of about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL.

In some embodiments, the final UF DF operation is carried out using a medium comprising a composition solution or formulation solution intended for the protein after the UF DF operation. For example, if the composition obtained from the final UF DF operation is a pharmaceutical formulation comprising the protein, the final ultrafiltration and diafiltration operation is carried out using a formulation solution. If the composition obtained from the final UF DF operation is a DS comprising the protein, the final UF DF operation is carried out using a composition solution intended for containing the protein. Consequently, in the embodiments wherein the composition obtained from the final UF DF operation comprises a buffer, the final UF DF operation is carried out using a medium (e.g., the composition solution or formulation solution) comprising a buffer. In the embodiments wherein the composition obtained from the final UF DF operation comprises a buffer with low buffer capacity, the final UF DF operation is carried out using a medium (e.g., the composition solution or formulation solution) comprising a buffer with low buffer capacity (e.g., buffer at a low concentration, for example from 2 mM to 10 mM, and a pH within the buffer capacity range of the buffer, or buffer at a pH that is outside the buffer capacity range of the buffer). In the embodiments wherein the composition obtained from the final UF DF operation comprises essentially no buffer, the final UF DF operation is carried out using a medium (e.g., the composition solution or formulation solution) comprising essentially no buffer. Unless otherwise clear from the context of its use, a "composition solution" or a "formulation solution" is a solution that does not itself contain the protein of interest but is used to make a formulation or composition comprising the protein. Suitable buffers and buffer concentrations are disclosed above.

In some embodiments, the final UF DF operation is carried out at a temperature of from about 20° C. to about 50° C. In some embodiments, the final UF DF operation is earned out at a temperature of from about 25° C. to about 40° C. In some embodiments, the final UF DF operation is carried out at a temperature of from about 30° C. to about 40° C.

Stabilizing Agents

In some embodiments, the method disclosed herein comprises adding one or more stabilizing agents or stabilizers to the preparation to increase, promote or maintain the stability of proteins of interest. In some embodiments, the stabilizer is an amino acid, a sugar, a polyol, an anti-oxidant, a chelating agent, a lipid or a lipid derivative, a salt, a polymer, an inert protein or polypeptide, a surfactant, a water-miscible co-solvent or a combination thereof. Nonlimiting examples of amino acid stabilizers that may be used in the methods disclosed herein include histidine, arginine, glycine, methionine, alanine, aspartic acid, lysine hydrochloride, proline, lysine, sarcosine, gamma-aminobutyric acid, and glutamic acid, or di- and tri-peptides comprising the amino acids. Nonlimiting examples of antioxidants include ascorbic acid, glutathione, vitamin E. and poly(ethylenimine). Nonlimiting examples of chelating agents include ethylenediaminetetraacetic acid (EDTA), diethylenetriaminepentaacetic acid (DTPA), citric acid, hexaphosphate, and thioglycolic ac d Nonlimiting examples of sugars include sucrose, trehalose, xylitol, maltose, dextrose, glucose, raffinose, and lactose. Nonlimiting examples of polyols include sugar alcohols (e.g., sorbitol, inositol, mannitol), glycerol, erythritol, caprylate, tryptophanate, and sarcosine. Nonlimiting examples of polymers and inert proteins include protamine sulfate, polygalactouronic acid, phytic acid, polyfumaric, polysebacic acid, PEG-poly(lysine), polyaspartic acid block copolymer, carboxyphenoxypropane sebacic acid copolymer, chitosan, chitin, palmitoyl glycol chitosan, glycated chitosan, NNN, trimethyl chitosan, chlorogenic acid chitosan, polymers of acylated amino acids, poly(ethyl acrylic acid), poly(propyl acrylic acid), long chain alkyl amine substituted poly (acrylic acid), proteinoids (condensation polymers of modified acylated amino acids), heparin, heparin sulfate, dextran sulfate, bases with conjugations such as PEG (e.g., PEG-succinate), polyrotaxanes, galacosylated poly(lysine), alpha-2-macroglobulin:poly(lysine), galactosylated poly(ethyleneimine), N-(beta-hydroxyethyl)-lactaminde, poly(amidoamine) dendrimers, steryl-poly (L-lysine), poly(phosphoesters), PEG-caprylic-capric triglycerides, sucrose laurate, Tocopheryl PEG-acetate, tocopheryl PEG-succinate, gelatin, lactoglobulin, scrum albumin (e.g., human serum albumin (HSA), bovine serum albumin (BSA), and recombinant HA), hyaluronic acid, polyvinylpyrrolidone (PVP), poly(lactic-co-glycolic acid) (PLGA), polyacrylic acid (PAA) and derivatives thereof (eg. Amphipol A8-35, PAA5-25C8-40C3, Carbopol® 934, Carbopol® 980), polyethylene glycol (PEG), hydroxyethyl (heta) starch, sulfated polysaccharides, polyamino acids, dextran, diethylaminoethyl-dextran, cyclodextrin and derivatives thereof (e.g., hydroxypropyl-beta-cyclodextrin, sulfobutyl ether-beta-cyclodextrin), polyethyleneimine (PEI), and carboxymethyl cellulose. Nonlimiting examples of salts include sodium chloride, sodium sulfate, sodium thiocyanate, potassium chloride, potassium phosphate, lactic acid salts (e.g., calcium lactate), dioleoylpropyl-trimethyl-ammonium chloride (DOTMA), sodium caprylat, cholesterol sulfate, protamine sulfate, and guanidine hydrochloride. Nonlimiting examples of lipids and lipid derivatives thereof include fatty acids (e.g., oleic acid), phospholipids and phospholipid derivatives, DEA phosphate, DEA cetyl phosphate, oleth 10 phosphate, oleth-10, oleth-10 phosphate, DEA cetyl phosphate, mannosylglycerate, polidocanol, sulfobetaine cholate, phospholipids, and C12-15 alcohols benzoate. Nonlimiting examples of surfactants include nonionic surfactants including polysorbate 20, polysorbate 40, polysorbate 60, polysorbate 80, poloxamer (e.g., Pluronic F68 and F127), PEG dodecyl ethers (e.g., Brij 35 and Brij 30), and PEG tert-octylphenyl ether (e.g., Triton X-100). Nonlimiting examples of water-miscible cosolvents include dimethyl sulfoxide (DMSO), dimethylformamide (DMF), dimethylacetamide (DMA), N-methyl pyrollidone (NMP), ethanol, PEG-40 castor oil, and camphorsulfonic acid (CSA). A combination of one or more stabilizers from the above list may be used in the method disclosed herein.

As can be appreciated by one skilled in the art, some of the stabilizers disclosed herein can also impact the pH of the preparation. For example, certain amino acids are acidic (e.g., aspartic acid and glutamic acid) or basic (e.g., lysine and arginine), and can function as an acid or base or can form a buffer with a corresponding base or acid. Similarly, certain acids or bases disclosed herein can also function as a stabilizer, e.g., ascorbic acid, citrate acid, hyaluronic acid and lactic acid have stabilizing properties.

In certain embodiments, the one or more stabilizers are added before the final UF DF operation. In certain embodiments, the one or more stabilizers are added after the final UF DF operation. In certain embodiments, the one or more stabilizers are added before the final UF DF operation, and then removed during the UF DF operation (e.g., using a formulation solution or composition solution that does not contain the stabilizers) such that the stabilizers are not present in the composition comprising the protein of interest that is obtained after the UT DF operation. Typically, such stabilizers can stabilize the protein of interest before and during the UF DF operation, but may not be suitable for administration to patients (e.g., humans), e.g., not included in the FDA's Inactive Ingredients Database, available fda-.gov/Drugs/InformationOnDrugs/ucm113978.htm.

Proteins

Proteins that may be prepared by the methods disclosed herein include therapeutic proteins such as those approved tor human therapeutic use by regulatory agencies (e.g., FDA and EMA). In certain embodiments, the therapeutic proteins are therapeutic antibodies include, but are not limited to, a chimeric antibody, a human antibody, a humanized antibody, a bispecific antibody, and a domain antibody (dAb) The methods disclosed herein is particularly useful for making compositions comprising proteins (e.g., therapeutic proteins) that are unstable.

Nonlimiting examples of therapeutic proteins that may be prepared by the methods disclosed herein include Aflibercept (Eylea®), Etanercept (ENBREL®), Epoetin alfa (EPO-GEN®), Pegtilgrastim (Neulasta®), Filgrastim (NEUPO-GEN®), darbepoetin alfa (Aranesp®), Dornase alfa (Pulmozyme®), IL-2 mutein Fc fusion protein (AMG592), Becaplermin (REGRANEX®), Alteplase (Activase®), Laronidase (Aldurazyme®), Alefacept (Amevive®), Interferon beta-1b (BETASERON®), Rasburicase (Elitek®), Asparaginase (Elspar®), Agalsidase beta (Fabrazyme®), Interferon alfacon-1 (INFERGEN®), Interferon alfa-2a (INTRON A®), Anakinra (Kineret®), Oprelvekin (NEUMEGA®), Denileukin diftitox (Ontak®), Peginterteron alfa-2a (PEGASYS®), Aldesleukin (Proleukin®), Dornase alfa (Pulmozyme®), Interferon beta-1a (Rebif®), Becaplermin (REGRANEX®), Reteplase (Retavase®), Interferon alfa-2 (Roferon-A®), Tenecteplase (TNKase®), and Drotrecogin alfa (Xigris®), Rilonacept (ARCALYST®), Romiplostint (Nplate®), methoxypolyethylene glycol-epoetin beta (MIRCERA®), C1 esterase inhibitor (Cinryze®), idursulfase (Elaprase®), alglucosidase alfa (Myozyme®), abatacept (ORENCIA®), galsulfase (Naglazyme®), palifermin (Kepivance®) and interferon gamma-1b (ACTIMMUNE®).

Nonlimiting exemplary antibodies that may be prepared using the methods disclosed herein include bevacizumab (Avastin®), cetuximab (Erbitux®), adalimumab (HUMIRA®), infliximab (Remicade®), rituximab (Rituxar®), natalizumab (Tysabri®), eculizumab (Soliris®), trastuzumab (Herceptin®), Alemtuzumab (Campath®), Arcitumomab (CEA-Scan), Imciromab Pentetate (Myoscint®), Capromab Pendetide (ProstaScint®), Abciximab (ReoPro®), Rituximab (Rituxan®), Basiliximab (Simulect®), Palivizumab (Synagis®), Omalizumab (Xoiair®), Daclizumab (Zenapax®), Muromonab-CD3 (Orthoclone OKT3®), Edrecolomab (Panorex®), golimumab (Simponi®), Certolizumab pegol (Cimzia®), ustekinumab (Stelara®), panitumumab (Vectibix®), tositumomab (Bexxar®), panitumumab (Victibix®), evolocumab (Repatha®), denosumab (Prolia®), romosozumab (Eventiy®), tezepelumab, anti-PAC1 (pituitary adenylate cyclase activating type 1) receptor antibody (WO2014/144632), anti-IL-15 antibody (WO2007/087384), bispecific antibody-peptide conjugate that targets BAFF and ICOS ligand (U.S. Pat. No. 9,458,241), human monoclonal antibody that inhibits c-fms and decreases tumor-associated macrophage (TAM) function (WO2009/026303), prezalumab (WO2007/011941), erenumab (Aimovig™, WO2010/075238), and bispecific T cell engager (BiTE) antibody constructs including blinatumomab (Blicyto®), anti-CD33 and anti-CD3 BiTE antibody construct, anti-EGFRvIII and anti-CD3 BiTE antibody construct, anti-DLL3 and anti-CD3 BiTE antibody construct, anti-CD19 and anti-CD3 BiTE antibody construct, anti-MSLN and anti-CD3 BiTE antibody construct, anti-CDH19 and anti-CD3 BiTE antibody construct, anti-FLT3 and anti-CD3 BiTE antibody construct, anti-DLL3 and anti-CD3 BiTE antibody construct, anti-CDH3 and anti-CD3 BiTE antibody construct, anti*CD70 and anti CD3 BiTE antibody construct, anti-PSMA and anti-CD3 BiTE antibody construct, and anti-BCMA and anti-CD3 BiTE antibody construct (as described in WO2008/119567 and WO2017/134140).

The methods disclosed herein have several surprisingly good properties. For example, the methods disclosed herein simplify manufacturing processes for making buffer-free protein compositions from a multiple-step process to a one-step process and reduce manufacture footprint. In addition, protein compositions prepared by the methods disclosed herein have improved stability (e.g., reduced protein aggregates, reduced protein degradation) compared to protein compositions prepared by the same methods without the pH adjusting step.

The invention will be more fully understood by reference to the following examples. The examples should not, however, be construed as limiting the scope of the invention.

EXAMPLES

Example 1 Preparation of Etanercept Compositions Using UF DF Operation without a Prior pH Adjusting Step These examples test whether protein compositions with appropriate pH may be obtained from a final UF DF operation without a prior pH adjusting step. The protein used in these examples was etanercept. Different preparations of etanercept in TMS (tris, mannitol, sucrose) were exchanged into test formulations using formulation solutions SAS_100NaCl and PASS and compared the final pH to the target pH.

Materials: Etanercept: 25 mg/mL, in TMS (10 mM Tris HCl, 4% mannitol, 1% sucrose, pH 7.4); SAS_100NaCl solution (100 mM NaCl, 25 mM L-arginine HCl, 1% sucrose, pH 6.3); PASS buffer (25 mM Phosphate, 100 mM NaCl, 25 mM L-arginine HCl, 1% sucrose, pH 6.3); 10,000 MWCO centripreps; a Mettler Toledo MP220 pH meter and Mettler Toledo InLab MicroProbe.

Methods: 25 mg/mL etanercept in TMS was concentrated to ~50 mg/mL by ultrafiltration using 30K MWCO Pellicon 3 cassettes on a Millipore Pellicon-2 mini system. The material was then diafiltered against SAS_100NaCl or PASS solution for 7 diavolumes, followed by concentration by ultrafiltration to 100 mg/mL.

Results:

A summary of the results is shown below in Table 1.

TABLE 1

| | | pH using various exchange solutions | | | |
|---|---|---|---|---|---|
| Method of Exchange | Sample Name | Filtration Solution pH | Pre-Method Exchange pH | Post Method pH | Number of Exchanges |
| UF DF | PASS, pH 6.3, 100 mg/mL | 6.34 | 7.56 | 6.34 | 7 Diafiltration volumes |
| UF DF | SAS_100NaCl, pH 6.3, 100 mg/mL | 6.38 | 7.56 | 6.98 | 7 Diafiltration volumes |

Conclusion: When the samples were ultrafiltrated/diafiltrated from a pre-exchange solution at pH 7.56 into the PASS buffer, the target pH of 6.34 was attained. However, when the samples were ultrafiltrated/diafiltrated into the SAS_100NaCl solution that contains no buffer, the pH of the post-UF DF material that was achieved was 6.98, which was higher than expected and was not close to the final target pH of 6.3.

In view of the above results, a multi-step process was developed to formulate a protein in a buffer-free solution with a particular pH starting from a pre-exchange solution having a different pH: 1) perform UF DF to the anticipate pH using buffered formulation, 2) use salt to displace buffer, and 3) maintain pH using buffer-free solution.

Example 2: Preparation of Etanercept Compositions Using UF DF Operation with a Prior pH Adjusting Step Introduction: The goal was to formulate etanercept in the SAS formulation solution that contains no buffer (120 mM sodium chloride, 25 mM L-arginine, 1% sucrose, pH 6.3). Since Example 1 demonstrated that a multi-step process was necessary to formulate etanercept in a formulation solution without buffer as it was difficult to attain the target pH of 6.3 using UF DF when starting from etanercept in a sample at pH 7.56, a different and simpler method of exchange into the SAS formulation was needed. Two methods were evaluated that utilized separate final UF DF starting material: 1) column 3 (AEX) intermediate pool as the starting material, and 2) Enbrel drug substance in PASS formulation buffer (PASS DS intermediate pool) as the starting material. Each method is described below and summarizes the development of a final UF DF unit operation step to produce 50 g/L SAS formulated etanercept, including preparation of SAS formulation solution, final UF DF load conditioning and processing.

Methods: The SAS formulation solution is composed of 120 mM sodium chloride, 25 mM L-arginine, 1% sucrose, pH 6.3. An SAS formulation solution was titrated to pH 6.3 using 10 N NaOH. The volume of titrant required to reach the specific pH range was 4.4 µL/L SAS formulation solution. During execution of the SAS final UF DF unit operation, following equilibration of the membranes at 10 L/m$^2$ with the SAS formulation solution, the pH of the permeate remained close to the pH of WFI rather than the pH of the SAS formulation solution. Without being bound to a particular theory, this is believed to be due to the low buffering capacity of the SAS formulation solution. The expected range for conductivity of the permeate following membrane equilibration using the range of the SAS formulation solution preparation is 12-16 mS/cm. A higher post equilibration pH than that of the SAS formulation solution is expected and should not raise concern or indicate that the membranes are not equilibrated.

AEX Intermediate Pool Starting Material: Prior to transferring the AEX intermediate pool into the retentate tank of an UF/DF tank, the pool was conditioned using 2 M HCl to a target pH of 6.3 (acceptable range 6.2-6.4). The volume of titrant required to reach the specific pH range was approximately 2.8 mL/L AEX intermediate pool.

Eight examples performed during development of the SAS final UF DF unit operation step, using AEX intermediate pool as the starting material, are listed in Table 2. Two parameters were investigated: the pH of the conditioned AEX intermediate pool and the pH of the SAS formulation solution. The first three runs were analyzed for pH, conductivity, osmolality, protein concentration, and product quality. Runs 4 through 7 were only measured for pH, conductivity, osmolality, and protein concentration in order to determine impact of formulation solution pH and load pH impact UF DF pool pH.

TABLE 2

| AEX Intermediate Pool Starting Material: Load, Exchange Solution, and final UF DF pool pH | | | |
|---|---|---|---|
| Run Number | Target Load pH | Target SAS | UF DF Pool pH |
| 1 | 6.3 | 6.3 | 6.26 |
| 2 | 6.3 | 6.3 | 6.33 |
| 3 | 6.3 | 6.3 | 6.22 |
| 4 | 6.3 | 5.6 | 6.22 |
| 5 | 6.2 | 5.3 | 6.06 |
| 6 | 6.4 | 7.3 | 6.94 |
| 7 | 6.2 | 5.6 | 6.14 |
| 8 | 6.4 | 6.5 | 6.43 |

Results: The product quality results for the final SAS UF DF pool, generated using AEX intermediate pool as the starting material, are shown in Table 3. The step yield for Run 1 was outside of the acceptance criteria; however, it was most likely an artifact of bench-scale processing and considered not significant to the conclusions of the study. All three final UF DF SAS runs also met acceptance criteria for product quality using SEC and HIC analysis, as described above.

TABLE 3

| AEX Intermediate Pool Starting Material: Final SAS UF/DF Pool Product Quality | | | | |
|---|---|---|---|---|
| Parameter | Acceptance Criteria | Final SAS UF/DF Pool | | |
| | | Run 1 | Run 2 | Run 3 |
| pH | 6.1-6.5 | 6.26 | 6.22 | 6.33 |
| Protein Concentration (mg/mL) | 49-51 | 50.08 | 49.68 | 49.90 |
| Step Yield (%) | 95-103 | 93.4 | 99.5 | 100.5 |

Conditioned AEX Intermediate Pool Stability

The conditioned AEX intermediate pool can be held for up to 52.6 hours at controlled room temperature (CRT). The pH of the pool during the hold is shown in FIG. 1.

UF/DF Pool Stability

Figure 2A:
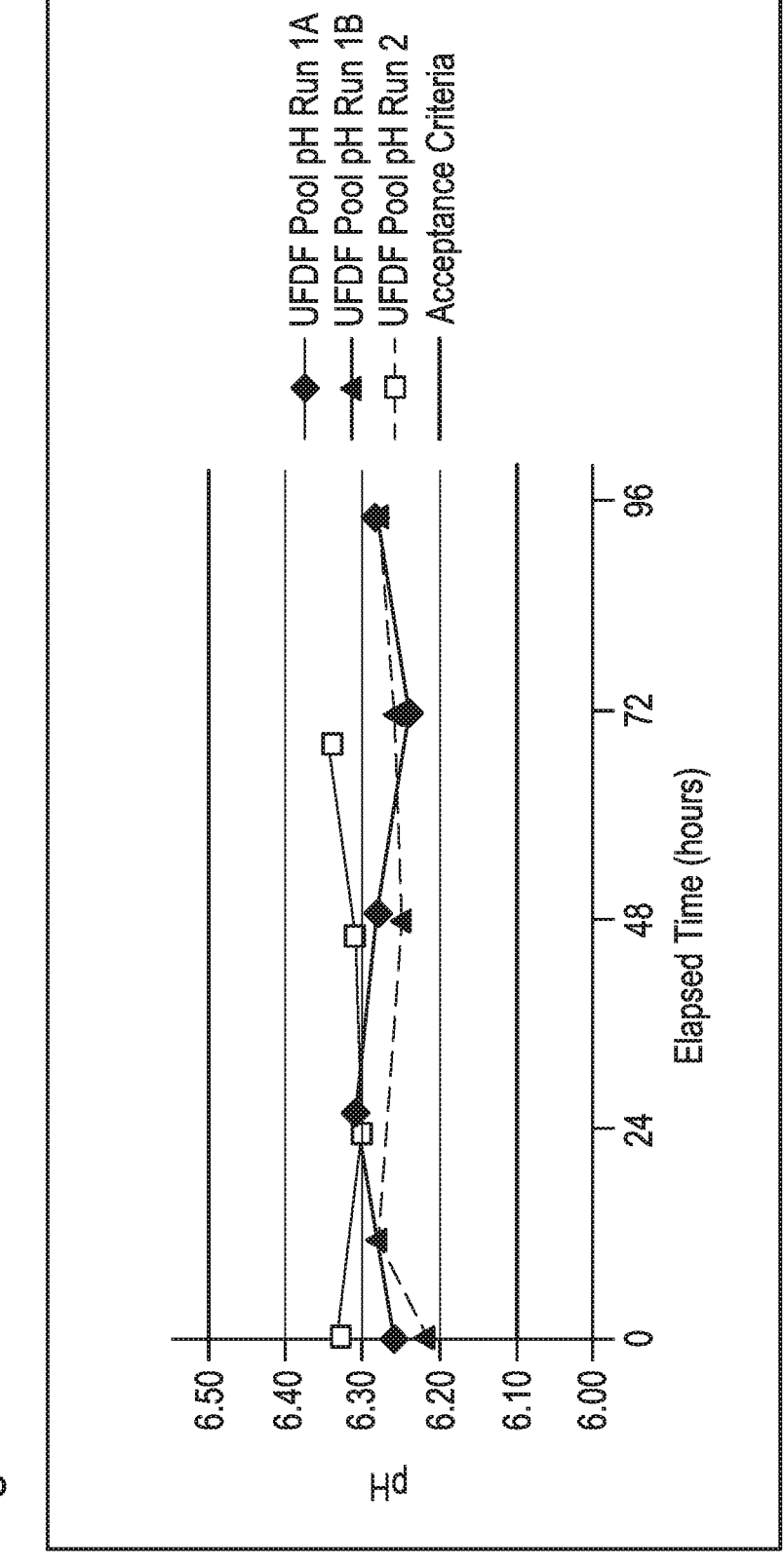
FIG. 2 shows the OF DF pool pH (A) and conductivity (B) stability at CRT in the assay of Example 1.
Figure 2B:
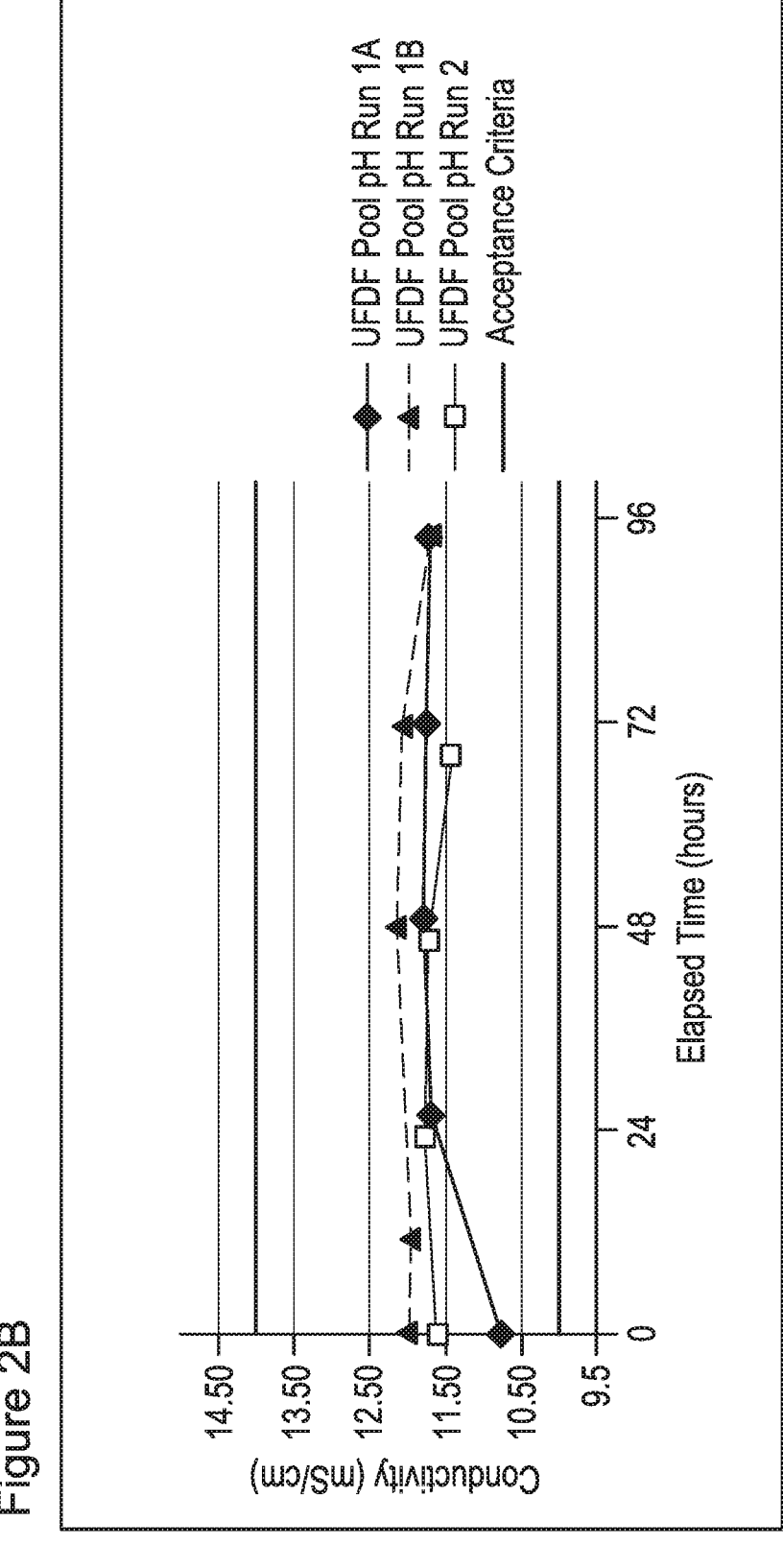

The final UF DF SAS pool, generated using AEX intermediate pool as the starting material, can be held for up to 96.3 hours at CRT. The pH and conductivity during the hold are shown in FIGS. 2 A and 2B. Over the 96.3 hour hold, the pH and conductivity remain within acceptable limits.

PASS DS Intermediate Pool Starting Material: No conditioning is required prior to transferring the PASS DS intermediate pool into the UF DF retentate tank because the PASS DS intermediate pool is already within the acceptable pH range. In addition, since the starting material is 50 mg/mL PASS formulated Enbrel DS, the pool does not need to be concentrated to 50 g/L because it is already at the correct concentration to perform diafiltration.

One example performed during development of the SAS final UF DF unit operation step, to evaluate starting material source, is listed in Table 4. This example utilized DS PASS intermediate pool as the starting material and was analyzed for pH, conductivity, osmolality, protein concentration, and product quality.

TABLE 4

PASS DS Intermediate Pool Starting Material: Load,
Exchange Solution, and final UF DF pool pH

| Run Number | Target Load pH | Target SAS Solution pH | UF/DF Pool pH |
|---|---|---|---|
| 1 | 6.3 | 6.3 | 6.23 |

Results: The product quality results for the final SAS UF DF pool, generated using PASS DS intermediate pool as the starting material, are shown in Table 5. The step yield for Run 1 was outside of the acceptance criteria; however, it was most likely an artifact of bench-scale processing and considered not significant to the conclusions of the study. The final SAS UF DF pool also met acceptance criteria for product quality using SEC and HIC analysis, as described above.

TABLE 5

PASS DS Intermediate Pool Starting Material:
Final SAS UF/DF Pool Product Quality

| Parameter | Acceptance Criteria | Final SAS UF/DF Pool Run 1 |
|---|---|---|
| pH | 6.1-6.5 | 6.23 |
| Protein Concentration (mg/mL) | 49-51 | 49.60 |
| Step Yield (%) | 95-103 | 105.7 |

PASS DS Intermediate Pool Stability

The PASS pool does not require conditioning prior to UF DF processing with SAS solution because this intermediate pool is already at the target pH (6.3). A pool hold study was not performed for this intermediate pool because the conditions of the pool were unchanged from Enbrel PASS DS. The pool can be held for up to 96 hours at 25° C.

UF DF Pool Stability

The final UF DF SAS pool, generated using PASS DS intermediate pool as the starting material, can be held for up to 96.3 hours at CRT. The pH and conductivity during the hold are shown in FIGS. 2 A and 2B. Over the 96.3 hour hold, the pH and conductivity remain within acceptable limits.

SAS Formulation Solution Stability

Figure 3A:
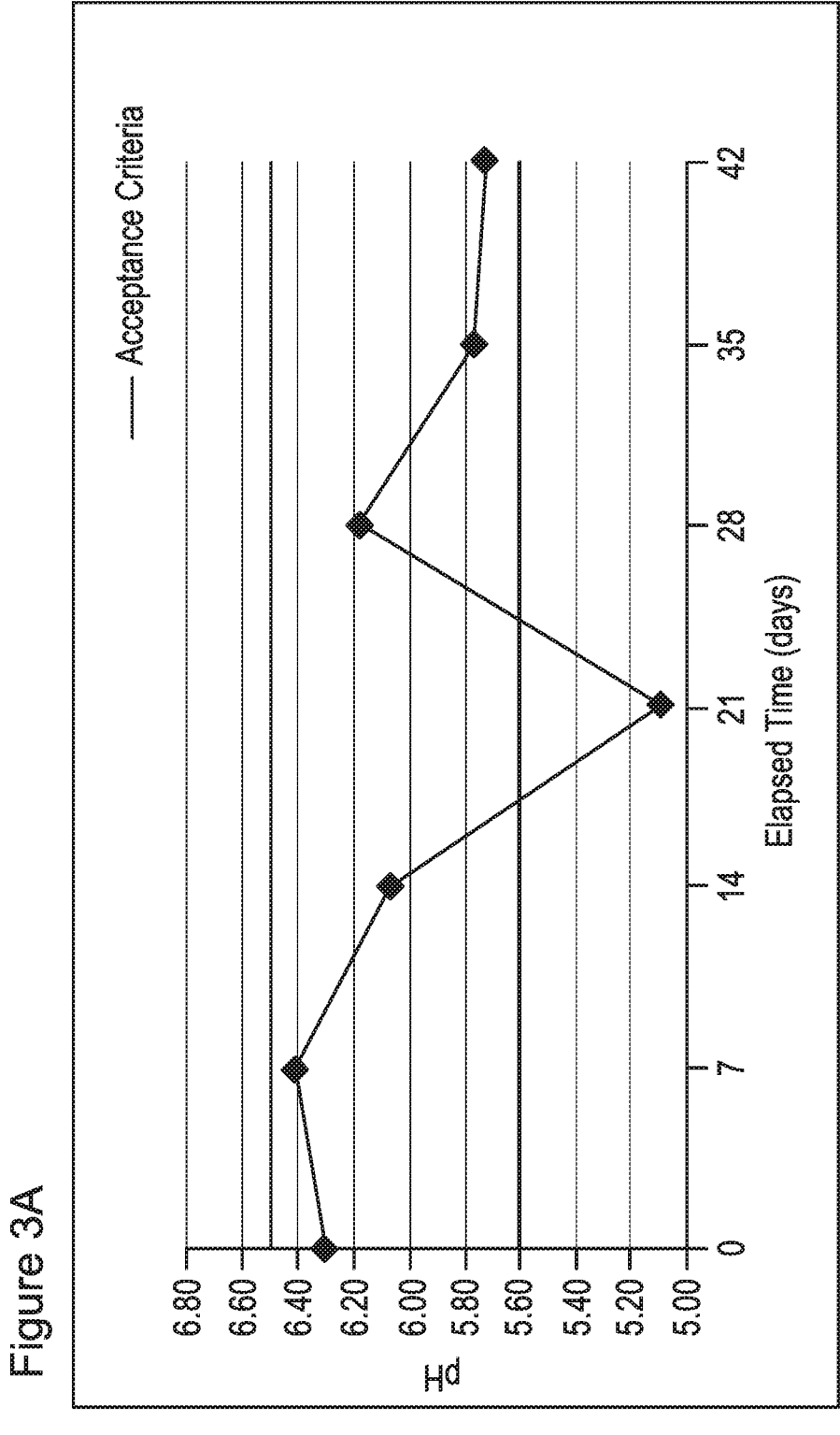
FIG. 3 shows the pH (A) and conductivity (B) stability of etanercept formulated in SAS solution in the assay of Example 1.
Figure 3B:
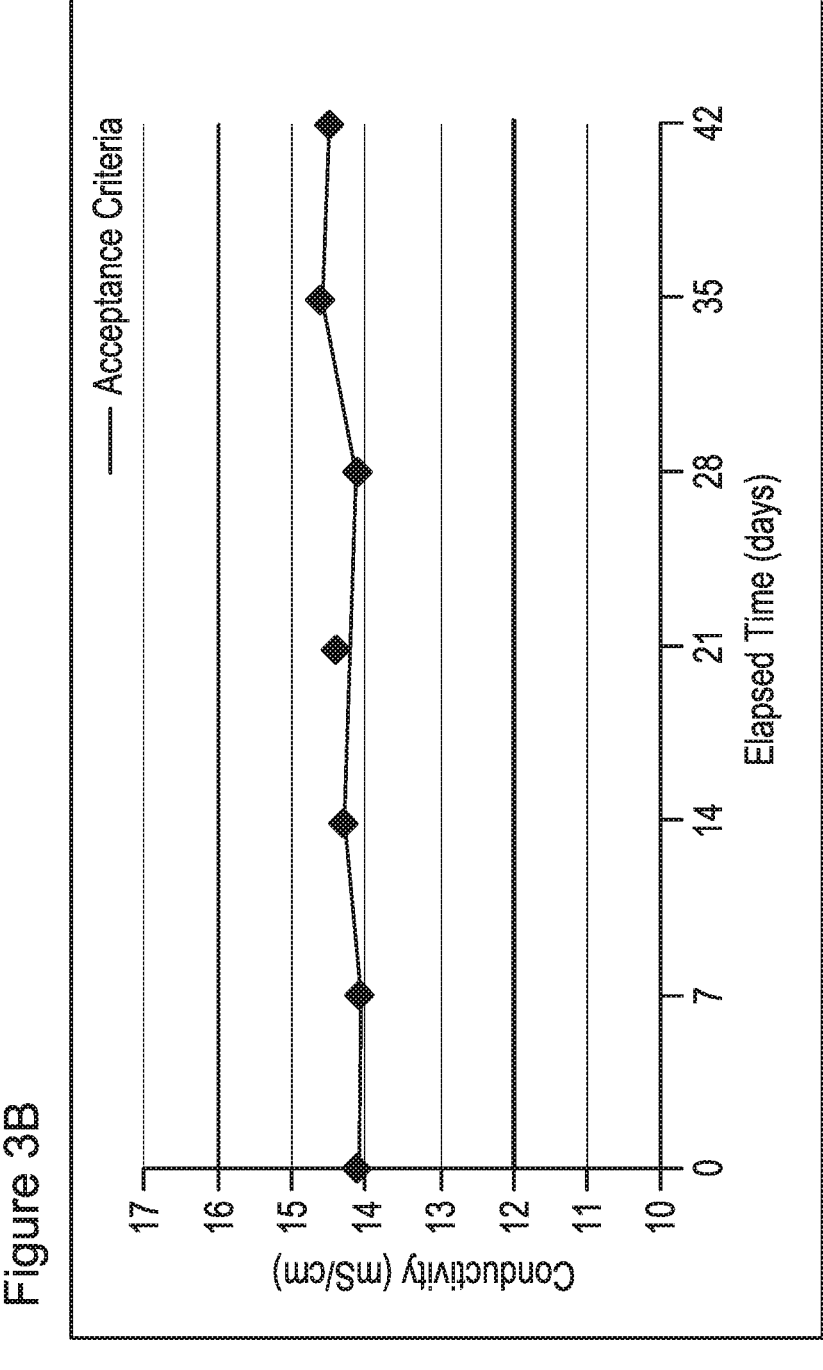

The SAS formulation solution can be held for up to 28 days at CRT. The pH and conductivity are shown in FIGS. 3 A and 3B. Over the 42 day hold in small scale stainless steel stability chambers with very small headspace, the SAS formulation solution is demonstrated to maintain a pH within 5.6 to 6.5. There was precipitation observed at the 35 day and 42 day time points. The 21 day time point measurement of 5.09 appears to be an outlier due to the fact that the subsequent time points are within the proposed acceptance criteria.

Conclusions: by incorporating a pH adjusting step prior to the final UF DF operation, the final UF DF unit operation can produce 50 g/L SAS formulation product and achieve consistent product quality compared to the PASS formulation product utilizing either AEX intermediate pool, or PASS DS intermediate pool, as the starting material. The following observations were also made: 1) the SAS solution can be held for at least 28 days at CRT and maintain a pH of 5.6 to 6.5, 2) the conditioned AEX intermediate pool can be held at CRT for at least 52.6 hours and maintain a pH of 6.3±0.1, and 3) the SAS formulated UF DF pool can be held at CRT for at least 96.3 hours and maintain a pH of 6.1 to 6.5 and a conductivity of 10 to 14 mS/cm.

Example 3: Preparation of Protein Formulations without Buffer Using a Single Step In order to develop a buffer-free formulation that could be scaled up for manufacturing purposes, the multi-step process described above in Example 1 was modified. Surprisingly, it was found that it is possible to convert a buffer-free formulation process from a three-step to a one-step process. In this approach, the pre-exchange material (e.g., VF pool material) is pH adjusted to anticipate the final formulation pH and then exchanged to the formulation solution using UF DF operations. The outcome is a buffer-free formulation, at a desired pH, with minimal to no salt present. This approach was found to work well, with minimal to no residual salt present following UF DF operations.

Compared to the multi-step process discussed in Example 1, the one-step process reduces the number of steps necessary for making protein compositions comprising no buffer (buffer-free compositions).

Example 4: Adjusting pH Prior to UF DF Operation Leads to Less Protein Aggregation Post UF DF Operation The protein used in the studies was adalimumab, and materials obtained from virus filtration (VF pool material) were used as the pre-exchange materials in the studies. In the studies, the pH of the VF pool materials was adjusted to or close to the target pH of pH 5.2 in the preparation of buffered and buffer-free formulations (see Table 6). The level of High Molecular Weight species present (HMW) was monitored using Size Exclusion Chromatography (SEC). The column used for this assay is a TSK-GEL, G3000SWXL, 5 um particle size, 7.8×300 mm size (Tosoh Bioscience, 08541), with the protein detected at a wavelength of 220 nm, and at a flow rate of 0.5 mL/min. Injection mass loads of protein were 35 µg.

Figure 4:
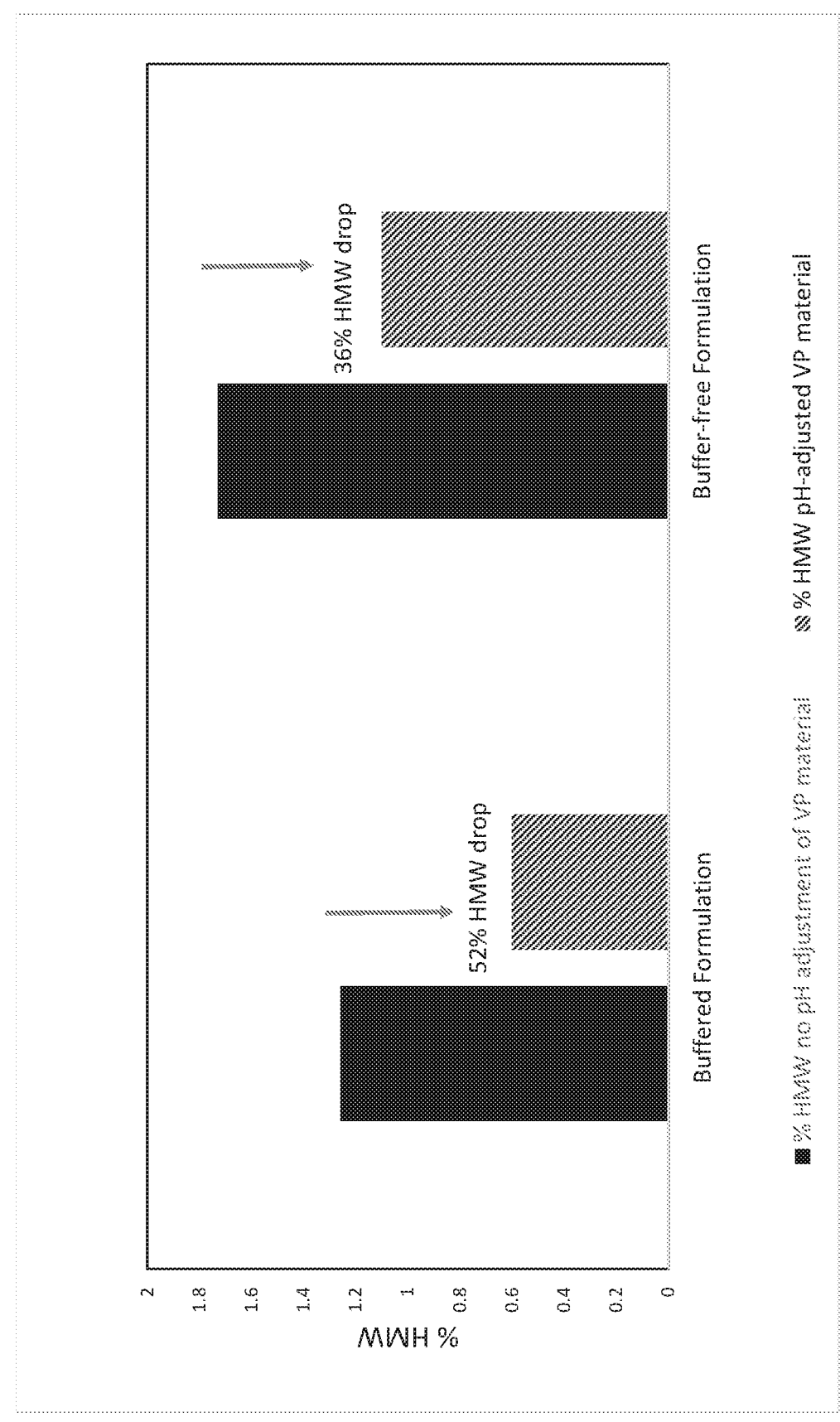
FIG. 4 shows the amount of HMW post OF DF operation in buffered and buffer-free formulations upon pH adjustment of the VF pool.

After the UF DF operation using the one step approach, the final formulation pH was consistent with the target pH. In this example, the final amount of aggregation present was reduced compared to the UF DF approach in which the pH of the VF pool material was not adjusted, as shown in FIG. 4. Additionally, FIG. 4 shows the drop in aggregation in both the buffer-free and buffered formulations with the pH adjusted to at or close to the target pH compared to the same samples prepared without adjustment of the pH in the VF pool material. Note that as shown in FIG. 4, aggregation after the UF DF step was cut by more than 50% compared to the level of aggregation obtained without adjusting the pH of the VF pool material.

In addition to changing the UF DF process for the preparation of buffer-free formulations from a three-step to a one-step manufacturing process, adjusting the pH before the final UF DF operation to the target pH reduced aggregation post UF DF. Furthermore, both buffered and buffer-free formulations can be prepared in this manner, by adjusting the pH of pre-exchange materials (e.g., VF pool material) to at or close to the target pH of the formulation. Taken together, the pH of both buffered and buffer-free formulations is maintained in this approach and it has also been shown to have beneficial effects on stability. This finding was not expected and is also considered surprising.

TABLE 6

Composition of buffered and buffer-free formulations.

| | Buffered Formulations | Buffer-Free Formulations |
|---|---|---|
| VF pool pH no adjusted | 10 mM lactate, 9% sucrose, 25 mM CaCl2, 0.006% Pluronic F 68 | 4% sorbitol, 25 mM CaCl2, 0.05% Pluronic F 68 |
| | | 4% sorbitol, 30 mM CaCl2, 0.05% Pluronic F 68 |
| VF pool pH adjusted | 10 mM lactate, 6% sucrose, 0.1% Pluronic F 68 10 mM lactate, 8.8% sucrose, 0.03% Pluronic F 68 | 4% sorbitol, 0.09% Polysorbate 20 |

Example 5: Preparation of Aflibercept Compositions Using UF DF Operation with a Prior pH Adjusting Step The goal of this example was to prepare aflibercept compositions with or without buffer using UF DF operation with a prior pH adjusting step. Formulations A-F were prepared but only Formulation A contains buffer. All formulation has a pH of pH 6.2.

Aflibercept was purified from a cell culture using CEX column into a 100 mM Na acetate, 300 mM NaCl, pH 5.0 at 3.6 mg/mL. The pH of the initial material was adjusted to 6.5 to account for the pH drift between the initial adjustment and post the buffer exchange that was observed in early studies. The protein was then concentrated to 40 mg/mL and buffer exchanged with the formulations as captured in Table 7. Surfactant was added to the different formulations post UF DF. The pH post the buffer exchange was tested and the samples were stored at the stress condition of 40° C. for up to two weeks. Protein stability was tested by SE-UHPLC to analyze the aggregation pattern post the buffer exchange and during storage.

TABLE 7

Formulations A-F

| Formu-lation | VEGF (mg/mL) | Buffer | Tonicity | Stabilizer | Surfac-tant | pH |
|---|---|---|---|---|---|---|
| A | 40 | 10 mM Sodium phosphate | 40 mM NaCl | 5% Sucrose | 0.03% PS20 | 6.2 |
| B | 40 | | | 5% Sucrose + 5% trehalose | 0.01% PS80 | 6.2 |
| C | 40 | | 5 mM NaCl | 5% Sucrose + 5% trehalose | 0.01% PS80 | 6.2 |
| D | 40 | | 10 mM NaCl | 5% Sucrose + 5% trehalose | 0.01% PS80 | 6.2 |
| E | 40 | | 20 mM NaCl | 5% Sucrose + 5% trehalose | 0.01% PS80 | 6.2 |
| F | 40 | | | 5% Sucrose + 5% trehalose | | 6.2 |

As can be seen in Table 8, the target pH was obtained within 0.1 pH units between the initial adjustment and post the buffer exchange. As the initial pH of the starting DS material was adjusted to pH 6.5, the pH of formulation A resulted in pH 6.4 instead of the initial target pH of 6.2. The difference between T=0 and following two weeks of storage at 40° C. was also at maximum 0.2 pH units, an insignificant pH shift in terms of potential impact on quality attributes, demonstrating again that the pH remained stable over storage at stress conditions for all tested formulations.

TABLE 8

Tested pH values post UF DF and following storage at 40°

| Formu-lation | Post Initial pH adjustment | T = 0 | T = 1 w@40° C. | Delta from T = 0 | T = 2 w@40° C. | Delta from T = 0 |
|---|---|---|---|---|---|---|
| A | 6.4 | 6.4 | 6.4 | 0.0 | 6.5 | 0.1 |
| B | 6.2 | 6.3 | 6.3 | 0.1 | 6.4 | 0.1 |
| C | 6.2 | 6.2 | 6.2 | 0.0 | 6.3 | 0.1 |
| D | 6.2 | 6.2 | 6.2 | 0.0 | 6.3 | 0.1 |
| E | 6.2 | 6.2 | 6.3 | 0.1 | 6.4 | 0.2 |
| F | 6.2 | 6.3 | 6.3 | 0.1 | 6.5 | 0.2 |

The results of the SE-UHPLC analysis are presented in Table 9. All buffer-free formulations, regardless of salt or surfactant presence exhibited a higher main peak percentage demonstrating reduced aggregation or increased stability in comparison to the formulation containing the buffering agent (formulation A). When comparing the aggregation levels between formulation B and F, with and without surfactant respectively, a comparable percent main peak is observed, demonstrating that aflibercept self-buffered formulations are stable with and without surfactant in terms of their aggregation by SE-UHPLC.

TABLE 9

SE-UHPLC percent main peak for Formulation A-F

| % Main Peak | T = 0 | T = 1 w @ 40° C. | Delta from T = 0 | T = 2 w @ 40° C. | Delta from T = 0 |
|---|---|---|---|---|---|
| A | 97.9 | 94.5 | 3.4 | 92.5 | 5.4 |
| B | 98.0 | 96.4 | 1.6 | 95.5 | 2.5 |
| C | 98.0 | 96.3 | 1.7 | 95.3 | 2.7 |
| D | 98.0 | 96.1 | 1.9 | 94.9 | 3.1 |
| E | 98.0 | 95.8 | 2.2 | 94.4 | 3.6 |
| F | 98.0 | 96.6 | 1.4 | 95.7 | 2.3 |

Figure 5:
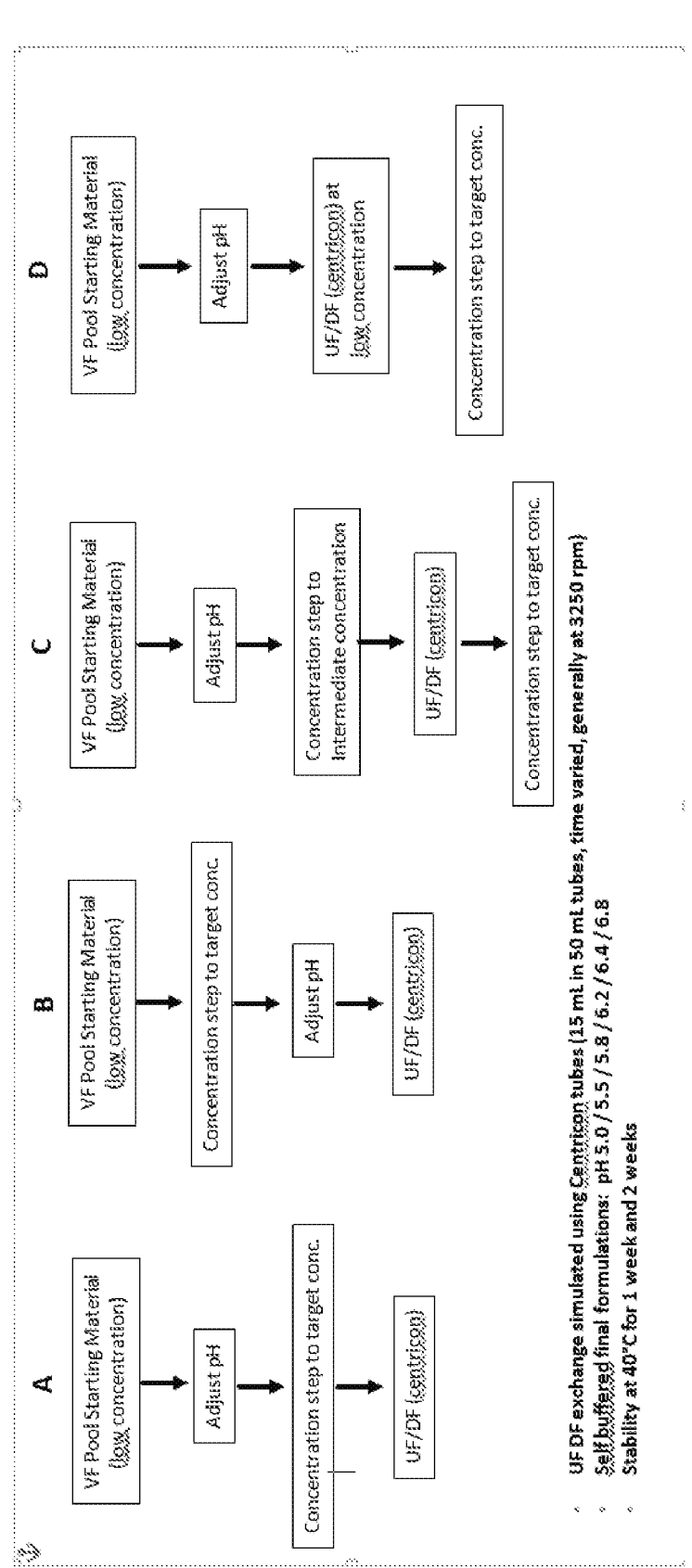
FIG. 5 shows four manufacturing options (Options A-D) for pH adjusting and concentrating steps.

Example 6: Adjusting the pH of the Pre-Exchange Material to the Target pH and then Concentrating the Protein was Preferred Aflibercept starting material (from the last step in manufacturing before the UF DF step), formulated in a buffer composed of 100 mM acetate, 300 mM NaCl, at pH 5, at a concentration of 3.6 mg/mL, was exchanged into the buffer using the four options shown in FIG. 5 (labeled A, B, C, and D) using 50 mL Centricon tubes to simulate the OF DF process. In approach A, 15 mL aliquots of starting material at 3.6 mg/mL was adjusted to pH 5.0, 5.5, 5.8, 6.2, 6.4 and 6.8, respectively, using 1M NaOH. Each pH-adjusted solution was then concentrated in 50 mL Centricon tubes to approximately 40 mg/mL. The pH-adjusted material at approximately 40 mg/mL was centricon-buffer exchanged into a solution with no buffer and containing 5% sucrose, 3.5% trehalose for at least 10 to 20 times the initial volume. After at least 20 times the initial volume exchange, the pH was checked and compared to the target pH. A similar approach was taken in B vs. A except that the starting material was concentrated to around 40 mg/mL initially, then the pH was adjusted to the levels shown in approach A with 1 M NaOH. Finally, the centricon-buffer exchange step was performed with at least 20 times the initial volume into an unbuffered solution containing 5% sucrose and 3.5% trehalose. Approach C was identical to that of approach B, with the exception that the concentration step and buffer exchange step was done at 10 mg/mL rather than at 40 mg/mL. Following the exchange step, the solution was concentrated to around 40 mg/mL in the 5% sucrose, 3.5% trehalose solution. Approach D performed a pH adjustment of the starting material at 3.6 mg/mL to pH 6.2, then a centricon-buffer exchange of the pH 6.2-adjusted material without a concentration step. After 20 times the exchange of the initial volume, the material was concentrated to around 40 mg/mL in the 5% sucrose, 3.5% trehalose solution. Only pH 6.2 was investigated in Approach D vs. pH 5.0, 5.5, 5.8, 6.2, 6.4 and 6.8 in Approaches A, B and C.

Figure 6:
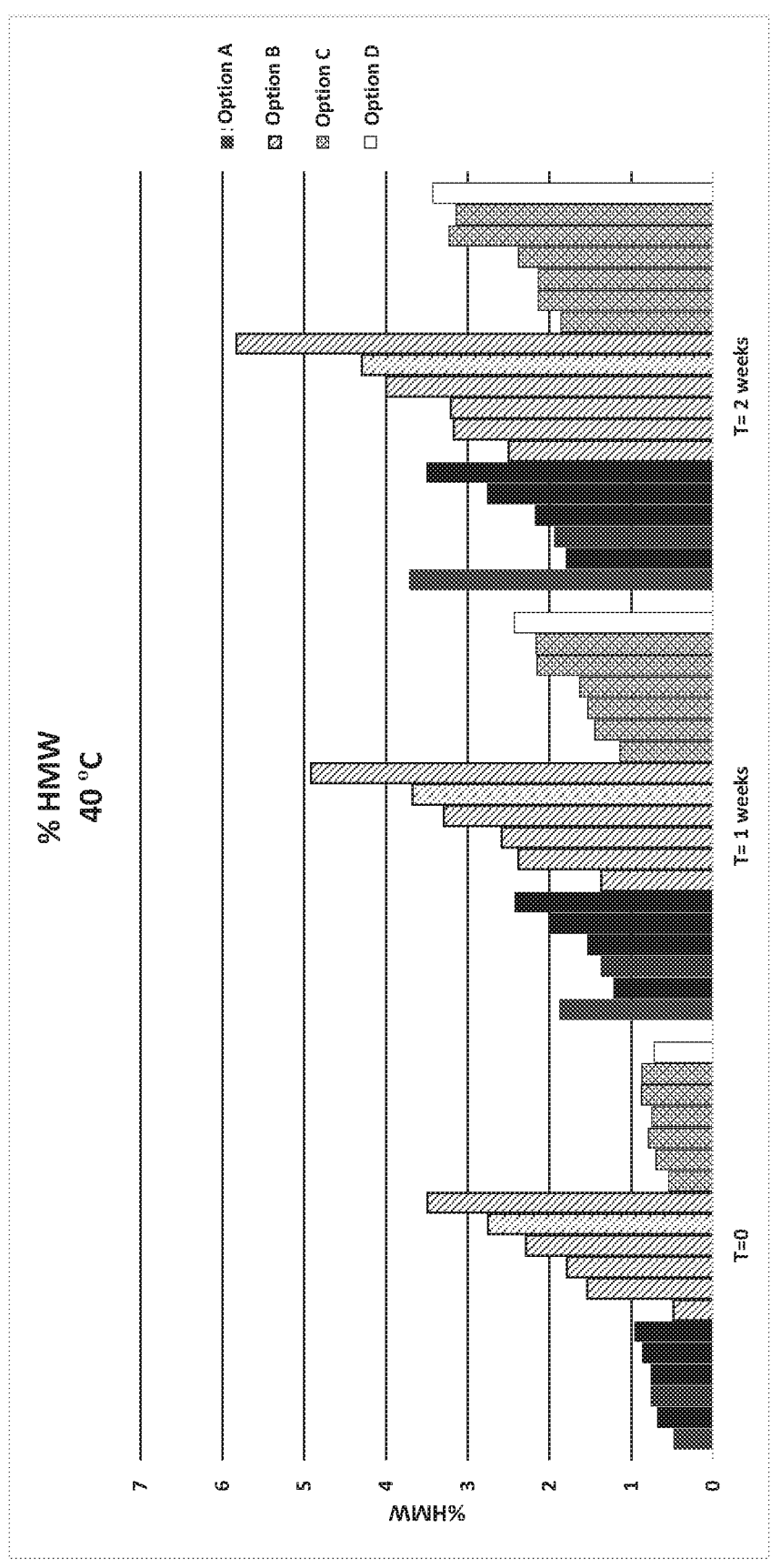
FIG. 6 shows % HMW of the aflibercept compositions prepared using the four manufacturing options.
Figure 7:
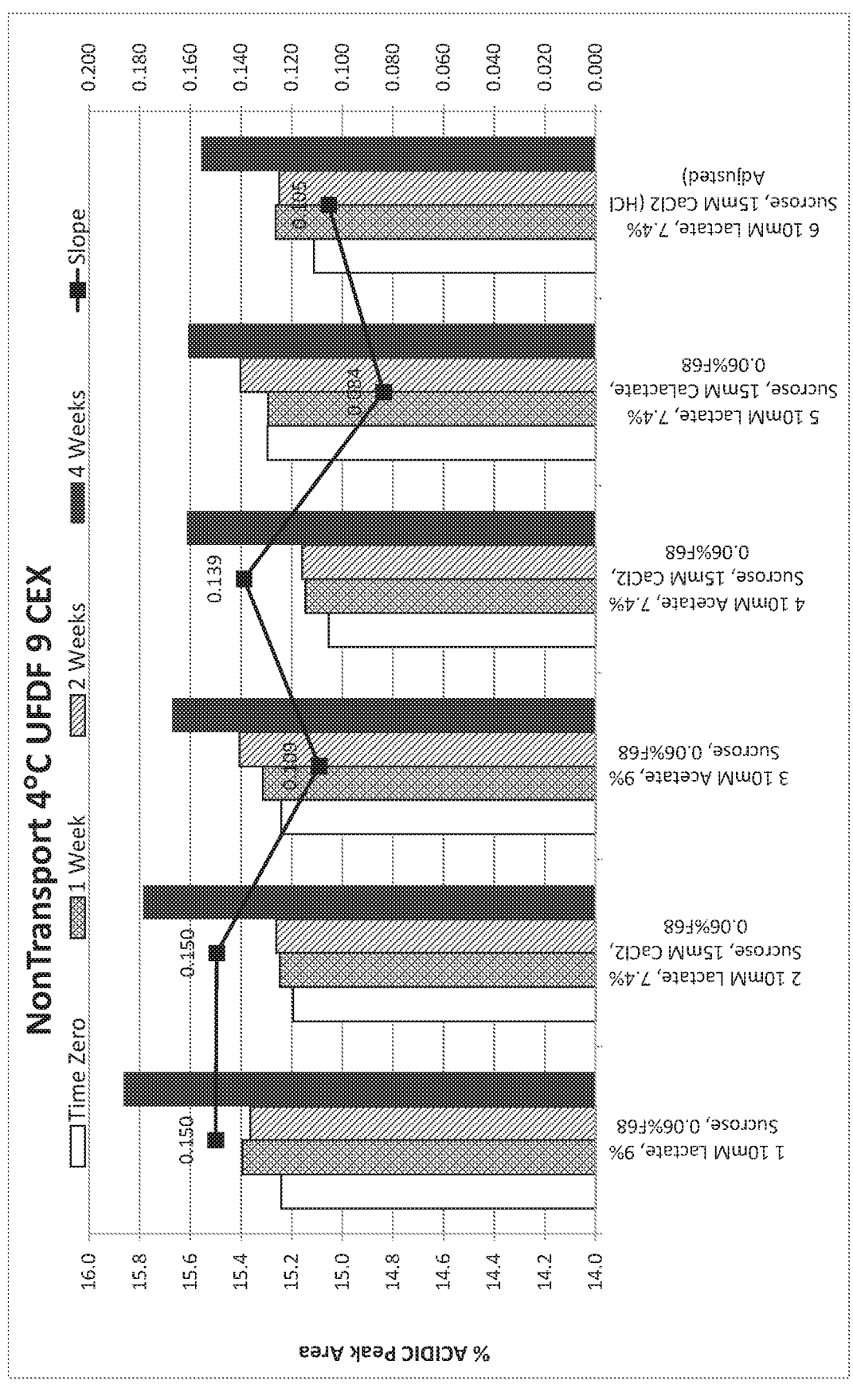
FIG. 7 shows the % acidic peak of the adalimumab formulations at 4° C. without transport measured by CEX-HPLC in Example 7.
Figure 8:
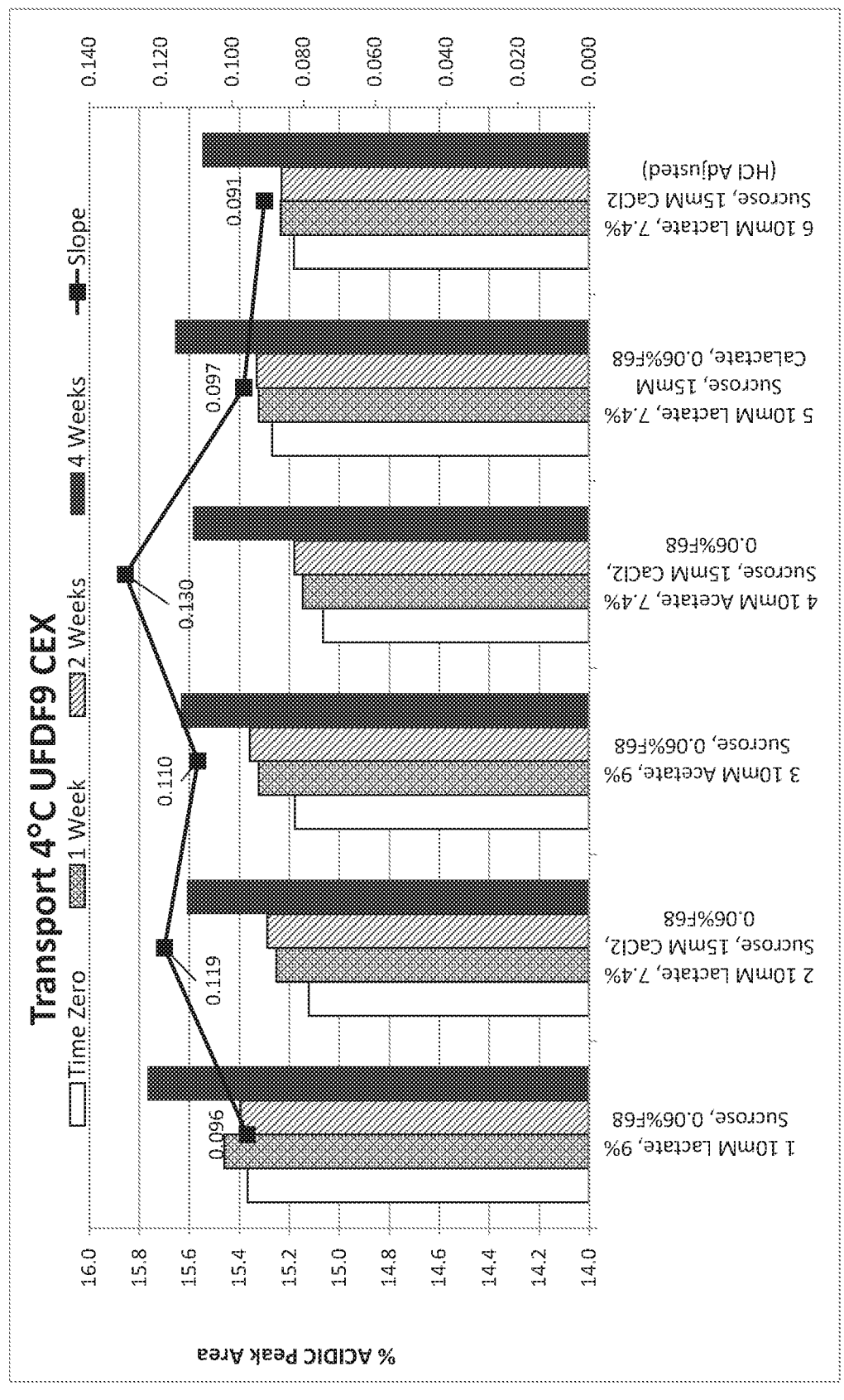
FIG. 8 shows the % acidic peak of the adalimumab formulations at 4° C. with transport measured by CEX-HPLC in Example 7.
Figure 9:
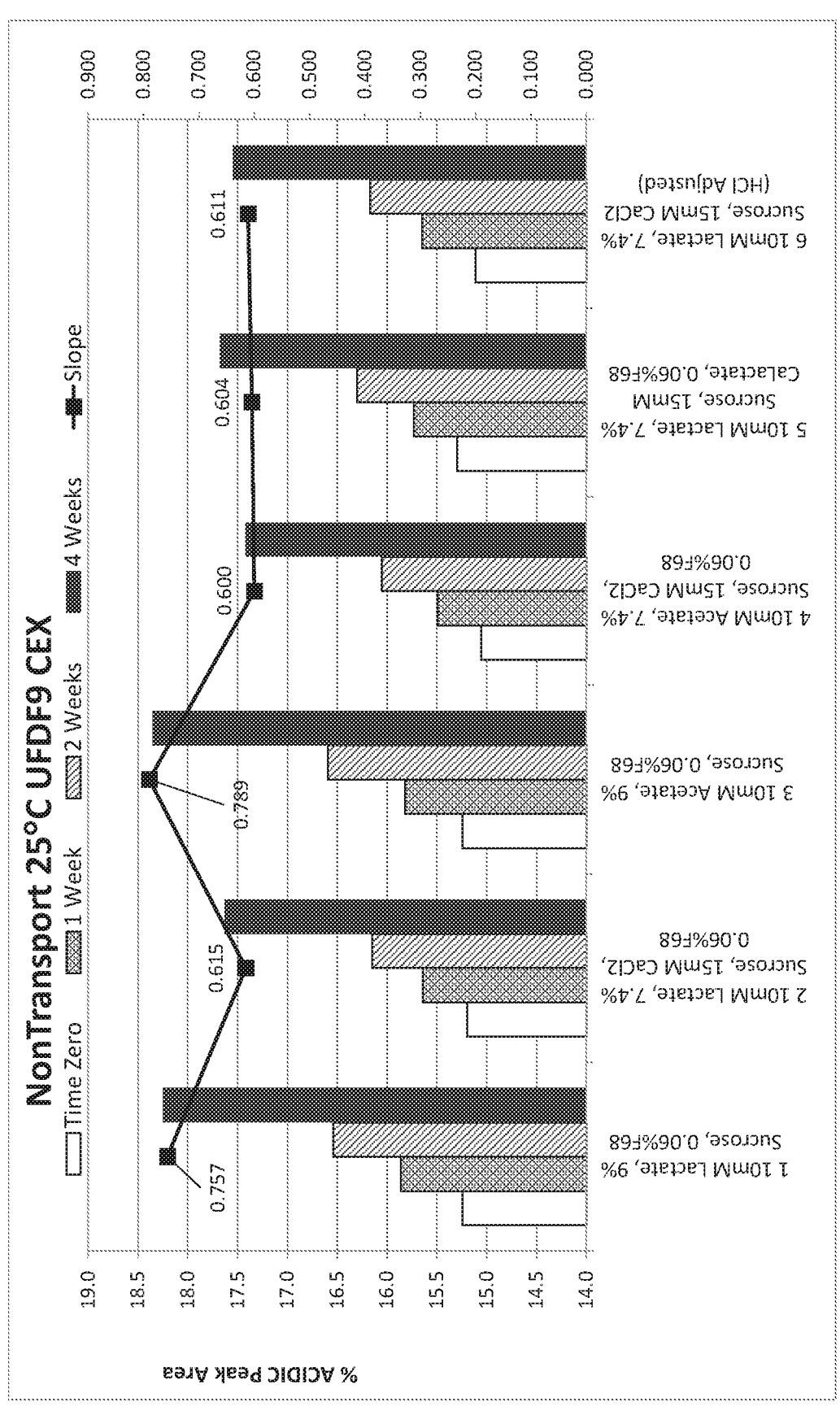
FIG. 9 shows the % acidic peak of the adalimumab formulations at 25° C. without transport measured by CEX-HPLC in Example 7.
Figure 10:
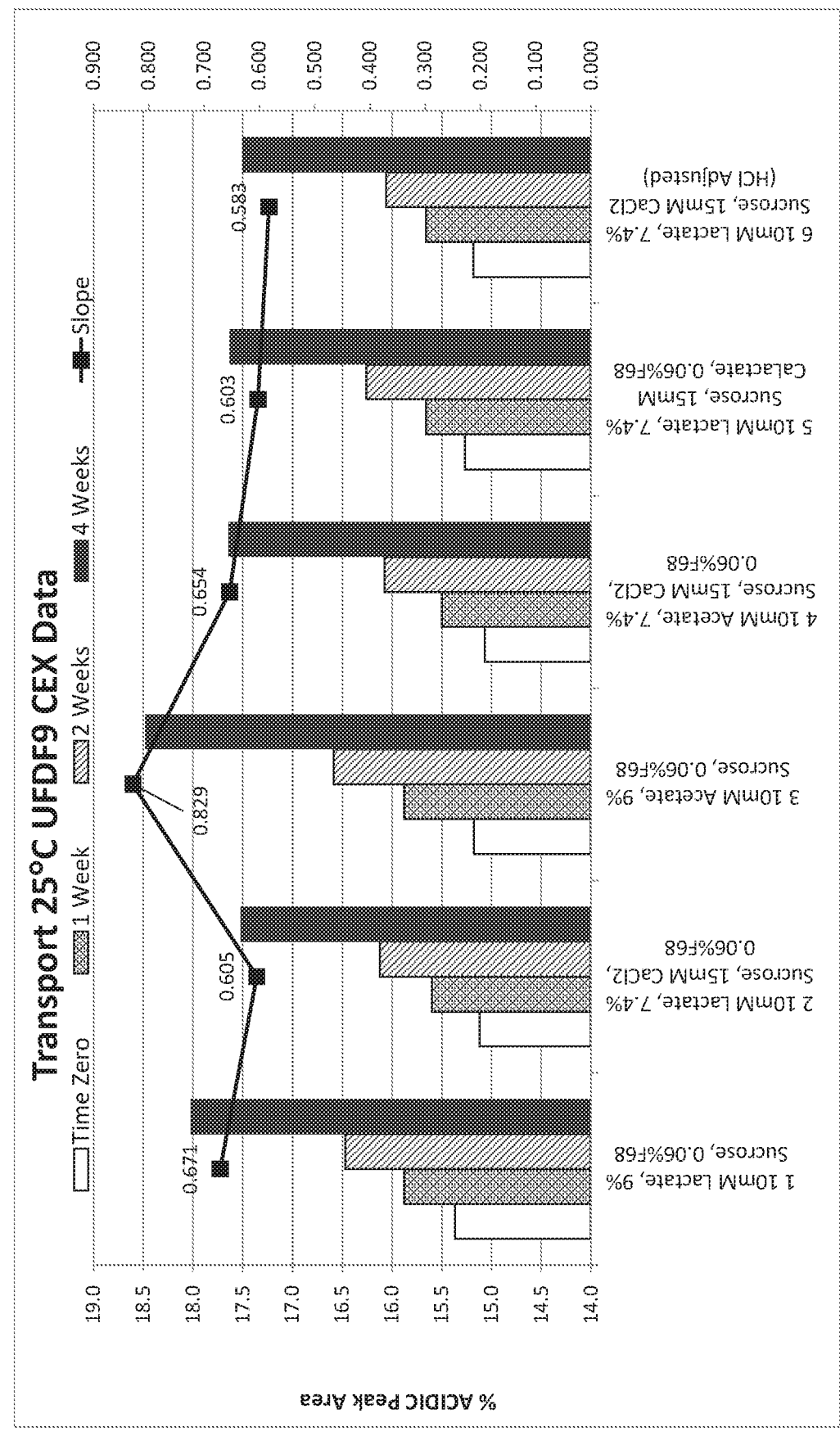
FIG. 10 shows the % acidic peak of the adalimumab formulations at 25° C. with transport measured by CEX-HPLC in Example 7.
Figure 11:
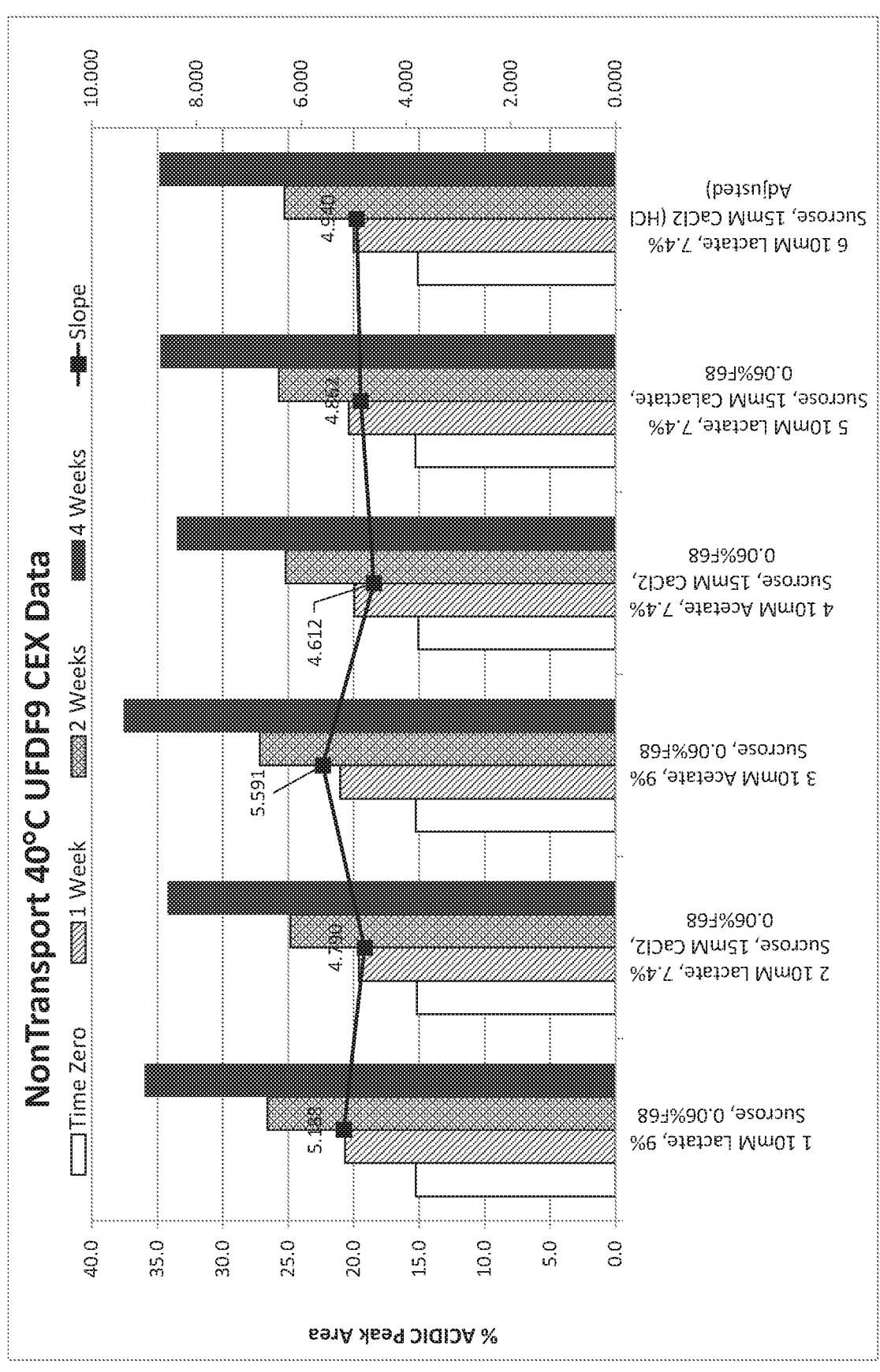
FIG. 11 shows the % acidic peak of the adalimumab formulations at 40° C. without transport measured by CEX-HPLC in Example 7.
Figure 12:
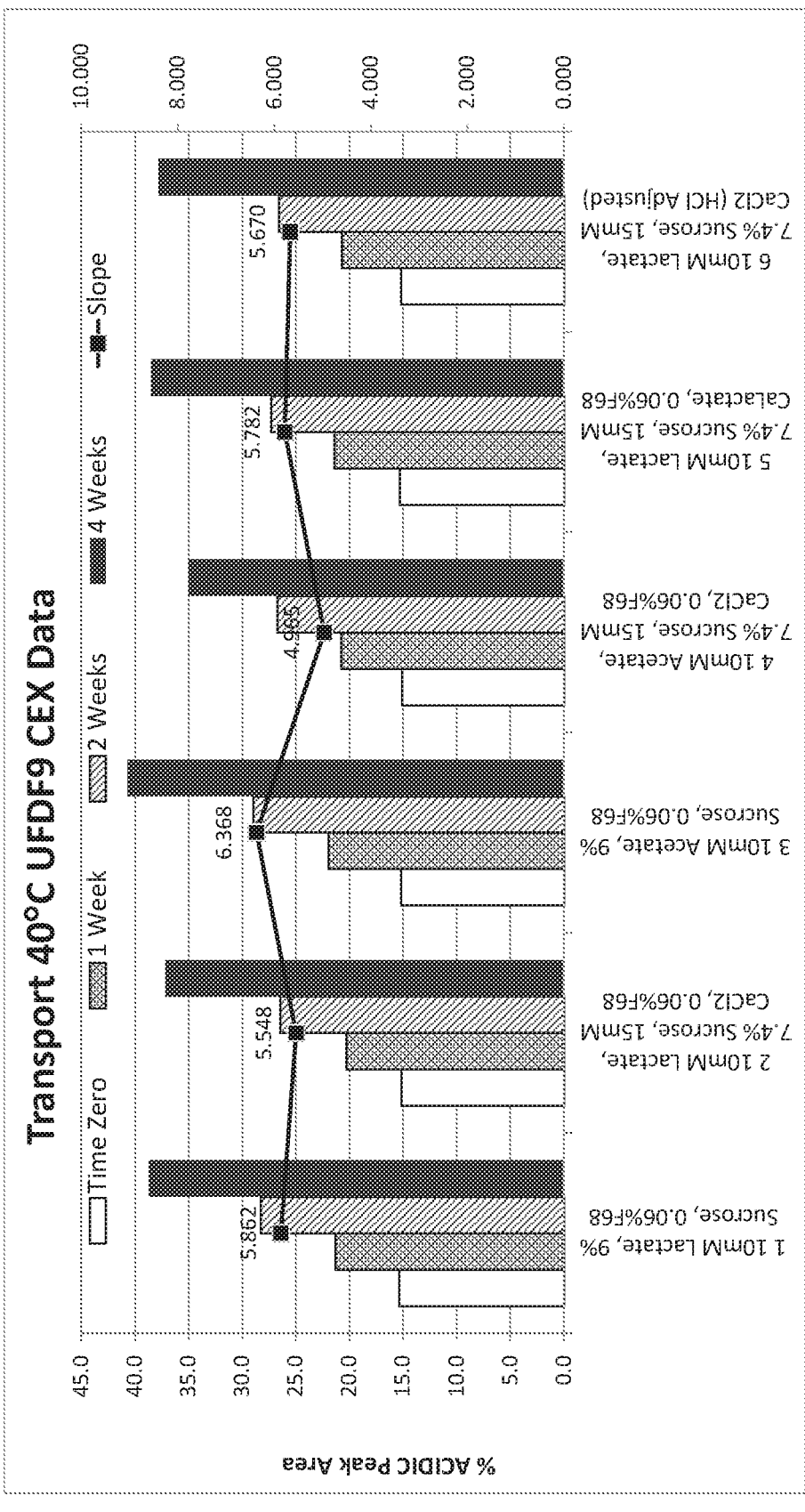
FIG. 12 shows the % acidic peak of the adalimumab formulations at 40° C. without transport measured by CEX-HPLC in Example 7.
Figure 13:
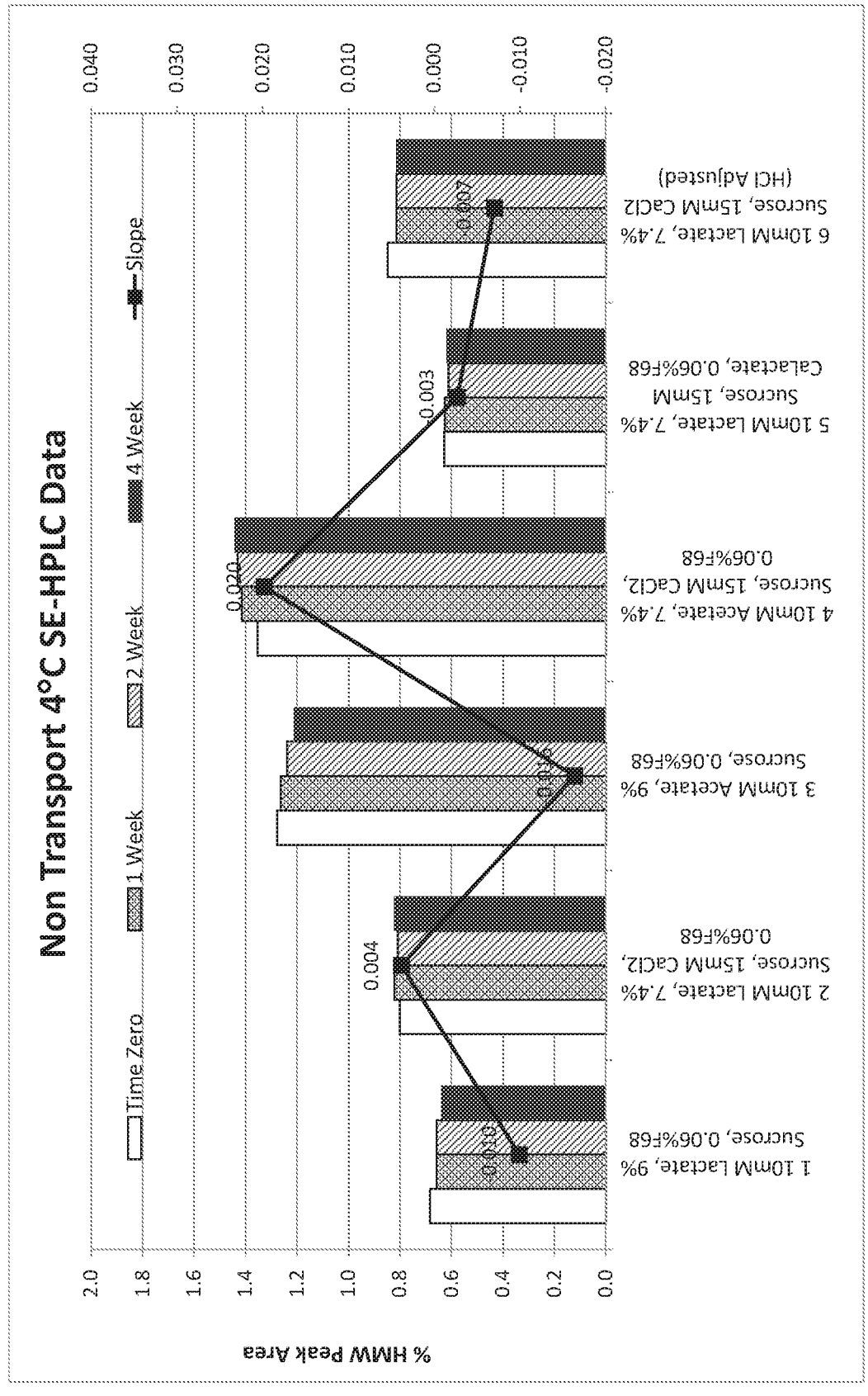
FIG. 13 shows HMWs of the adalimumab formulations at 4° C. without transport measured by SE-HPLC in Example 7.
Figure 14:
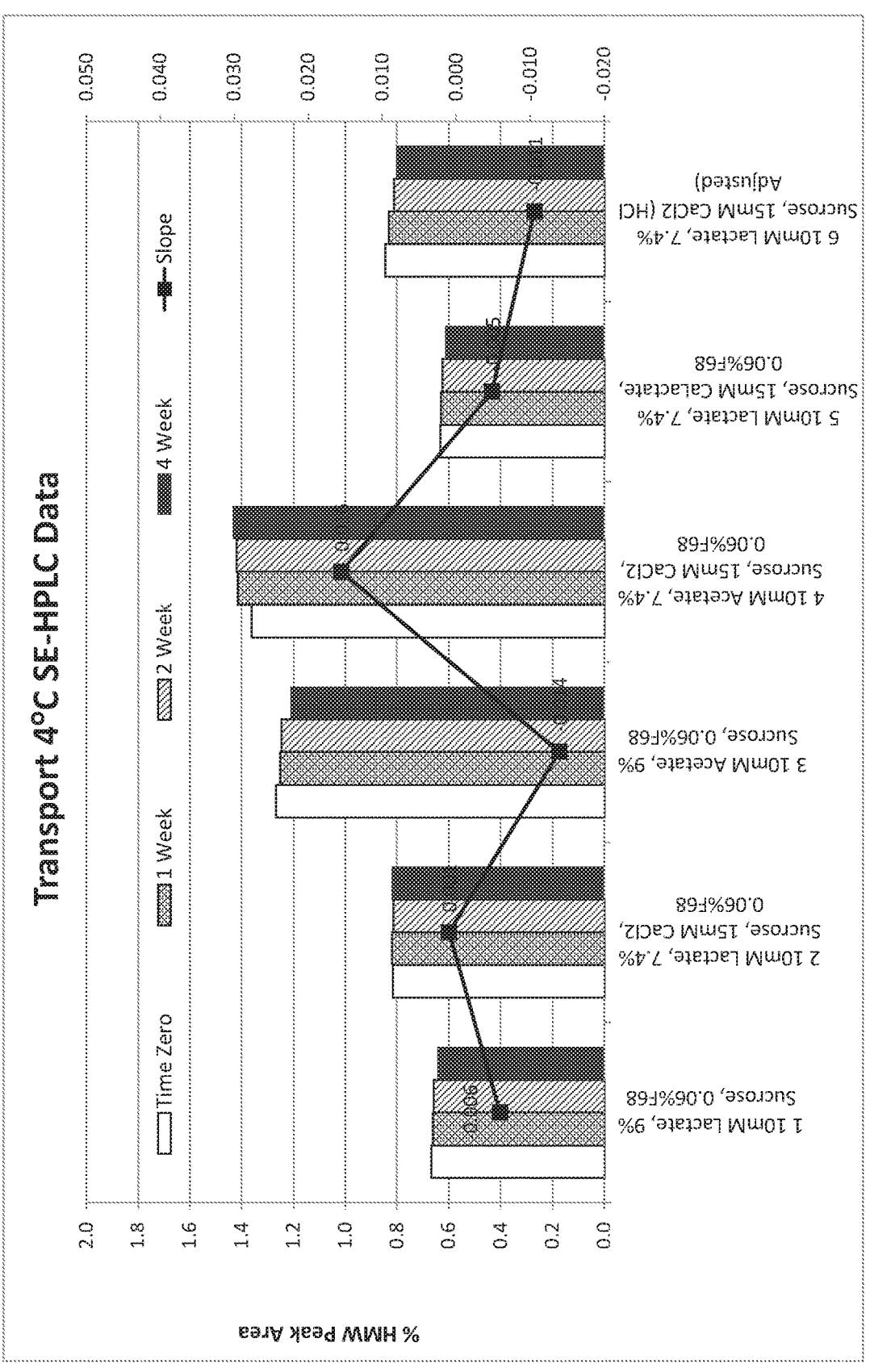
FIG. 14 shows HMWs of the adalimumab formulations at 4° C. with transport measured by SE-HPLC in Example 7.
Figure 15:
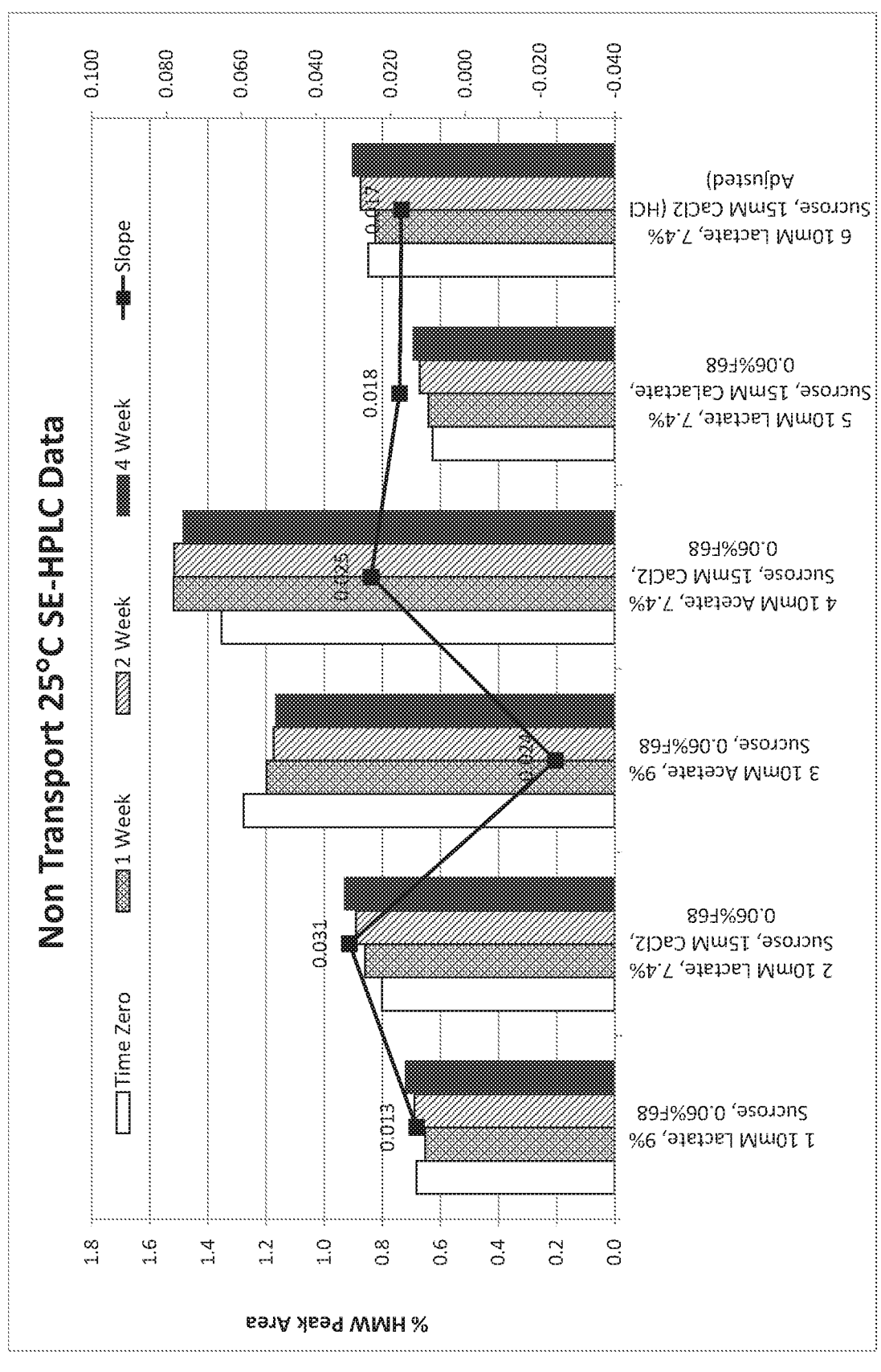
FIG. 15 shows HMWs of the adalimumab formulations at 25° C. without transport measured by SE-HPLC in Example 7.
Figure 16:
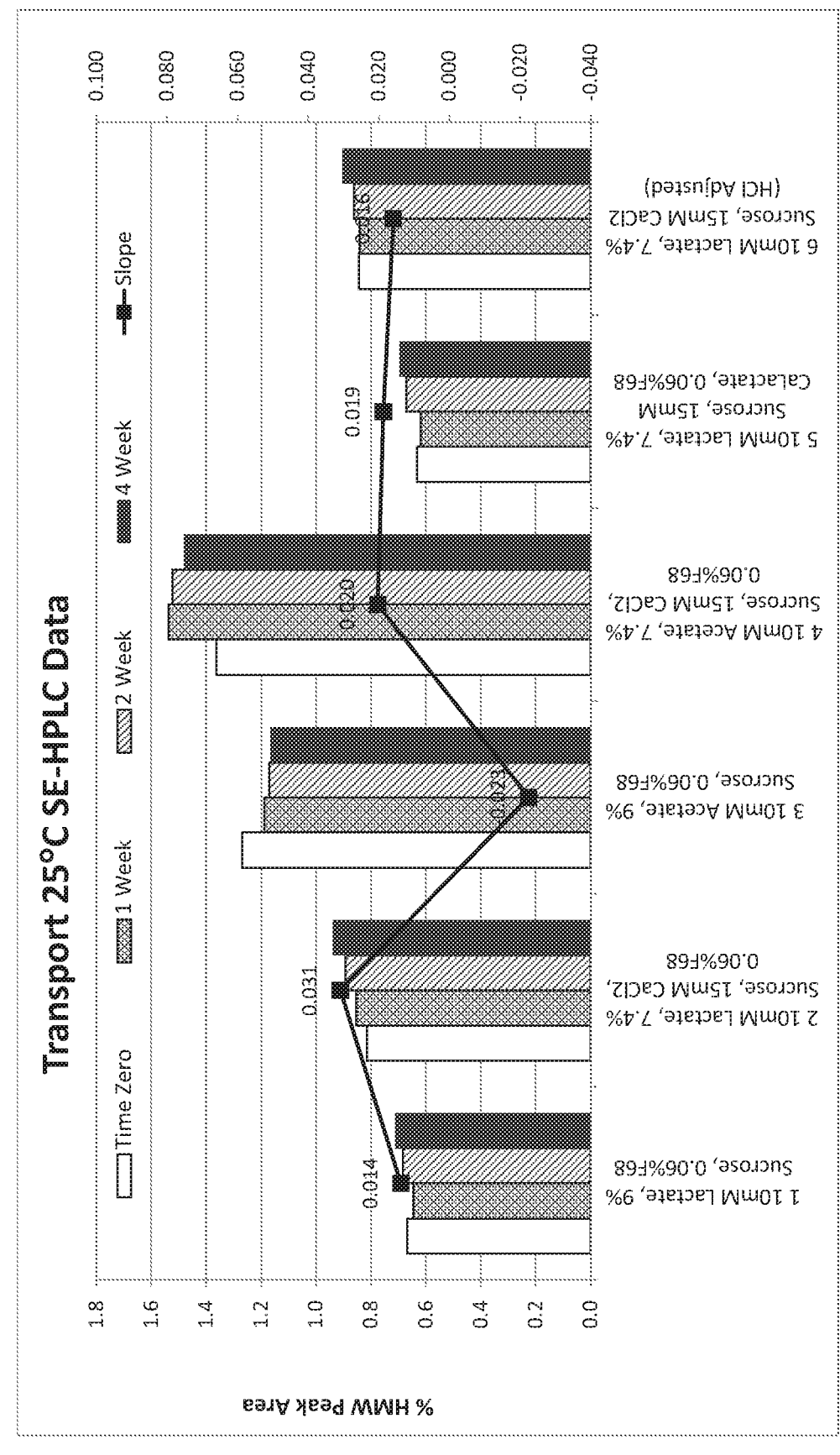
FIG. 16 shows HMWs of the adalimumab formulations at 25° C. with transport measured by SE-HPLC in Example 7.
Figure 17:
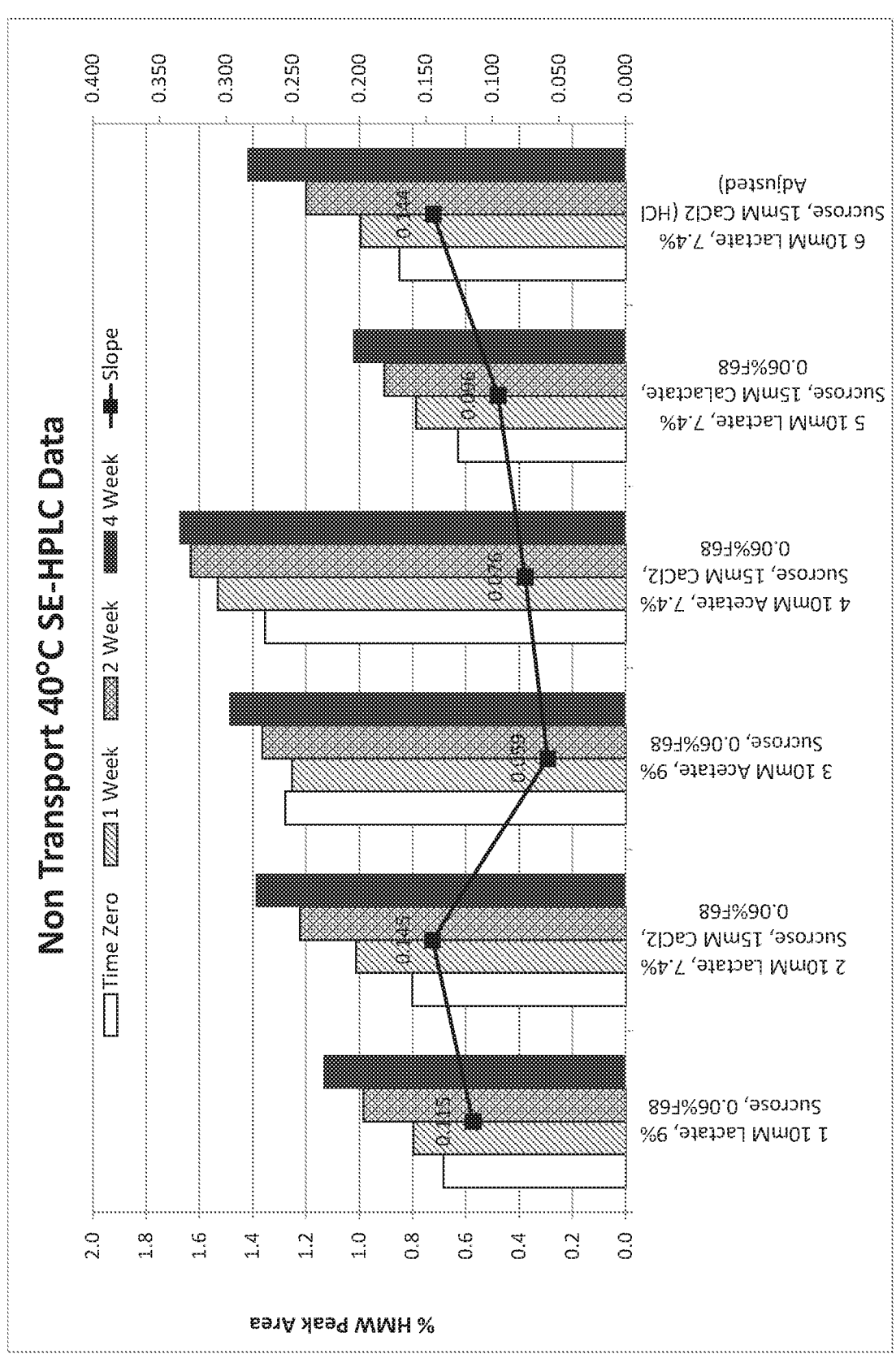
FIG. 17 shows HMWs of the adalimumab formulations at 40° C. without transport measured by SE-HPLC in Example 7.
Figure 18:
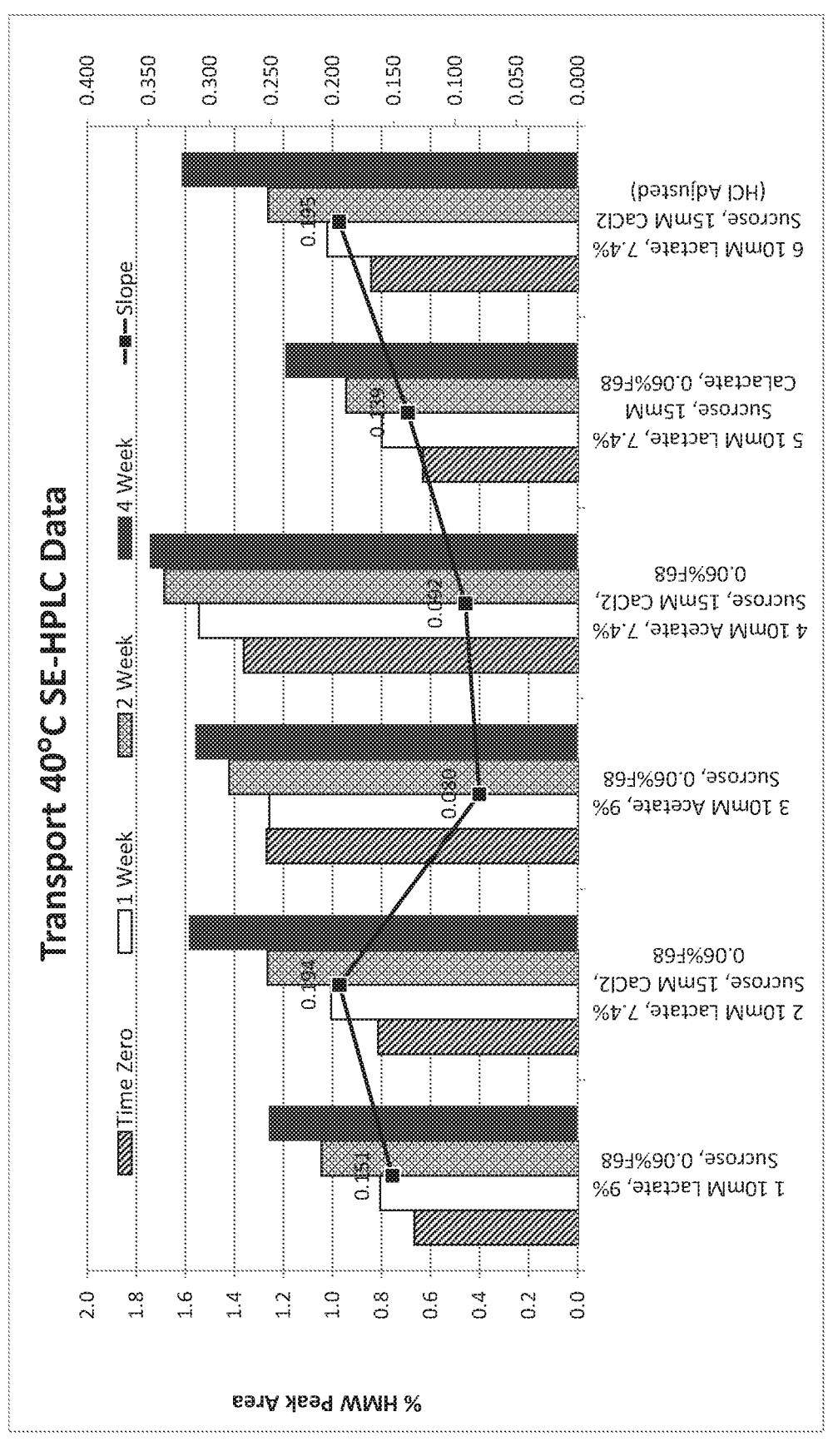
FIG. 18 shows HMWs of the adalimumab formulations at 40° C. with transport measured by SE-HPLC in Example 7.

After the buffer exchange into the 5% sucrose, 3.5% trehalose solution to create buffer-free formulations as described in approaches A through D, stability was assessed using Size Exclusion Chromatography (SEC) and the level of High Molecular Weight species present (HMW) monitored is shown in FIG. 6. The column used for this assay was a Waters BEH200, 4.6×250 mm, 1.7 μm particle size, with the protein detected at a wavelength of 280 nm, and at a flow rate of 0.4 mL/min. Injection mass loads of protein were 60 μg. As shown in FIG. 6, Options A and C resulted in less % HMW after simulated UF DF operations. This was demonstrated over a broad pH range, from pH 5 to 6.8. Option A was selected as the preferred option for scale up conditions.

Example 7: Preparation of Adalimumab Compositions Using UF DF Operation with a Prior pH Adjusting Step Several adalimumab formulations (formulations 18A-18F) were prepared, as shown in Table 10. As shown in the table, lactic acid and calcium hydroxide or acetic acid and HCl were used to adjust the pH prior to UF DF operations.

meaningful. After one month at 25° C. and at 40° C., the lowest rates of growth was observed in formulations containing calcium chloride or calcium lactate (formulations 18B, 18D, 18E, 18F).

Stability also was assessed by measuring HMWS by SE-HPLC after 0 days, after transport, and after storing the non-transported and transported samples at 4° C., 25° C., or 40° C. for 1, 2, and 4 weeks. The results are shown in FIGS. 13-18. At time zero and after 1 month at 4° C., the lowest amount of HMWS is observed in the lactic acid formulation with 9% sucrose and in the lactic acid formulation with 7.4% sucrose and 15 mM calcium lactate (formulations 18A, 18E). Although the rates of growth vary to a small extent at both 25° C. and 40° C., the amount of HMWS after 1 month at 25° C. and 40° C. is lowest in the same two formulations (18A, 18E) with the lowest amount of HMWS identified at time zero. As a general trend, formulations adjusted with lactic acid had lower amounts of HMWS than formulations adjusted with HCl and acetic acid prior to UF DF operations. Likewise, lactic acid buffered formulations are in general more stable.

Figure 19:
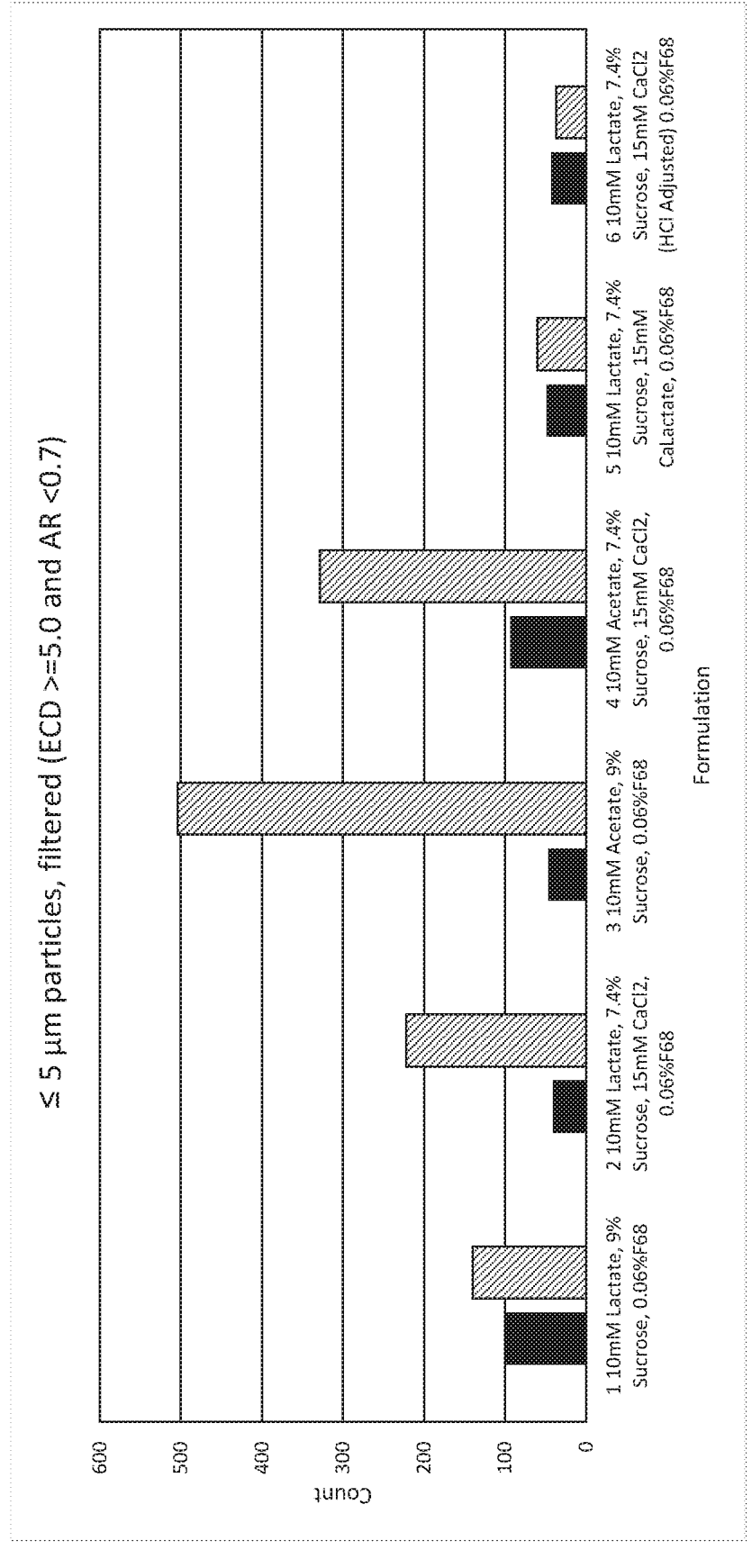
FIG. 19 shows the count of 5 μM sub-visible particles in the adalimumab formulations measured by MFI in Example 7.
Figure 20:
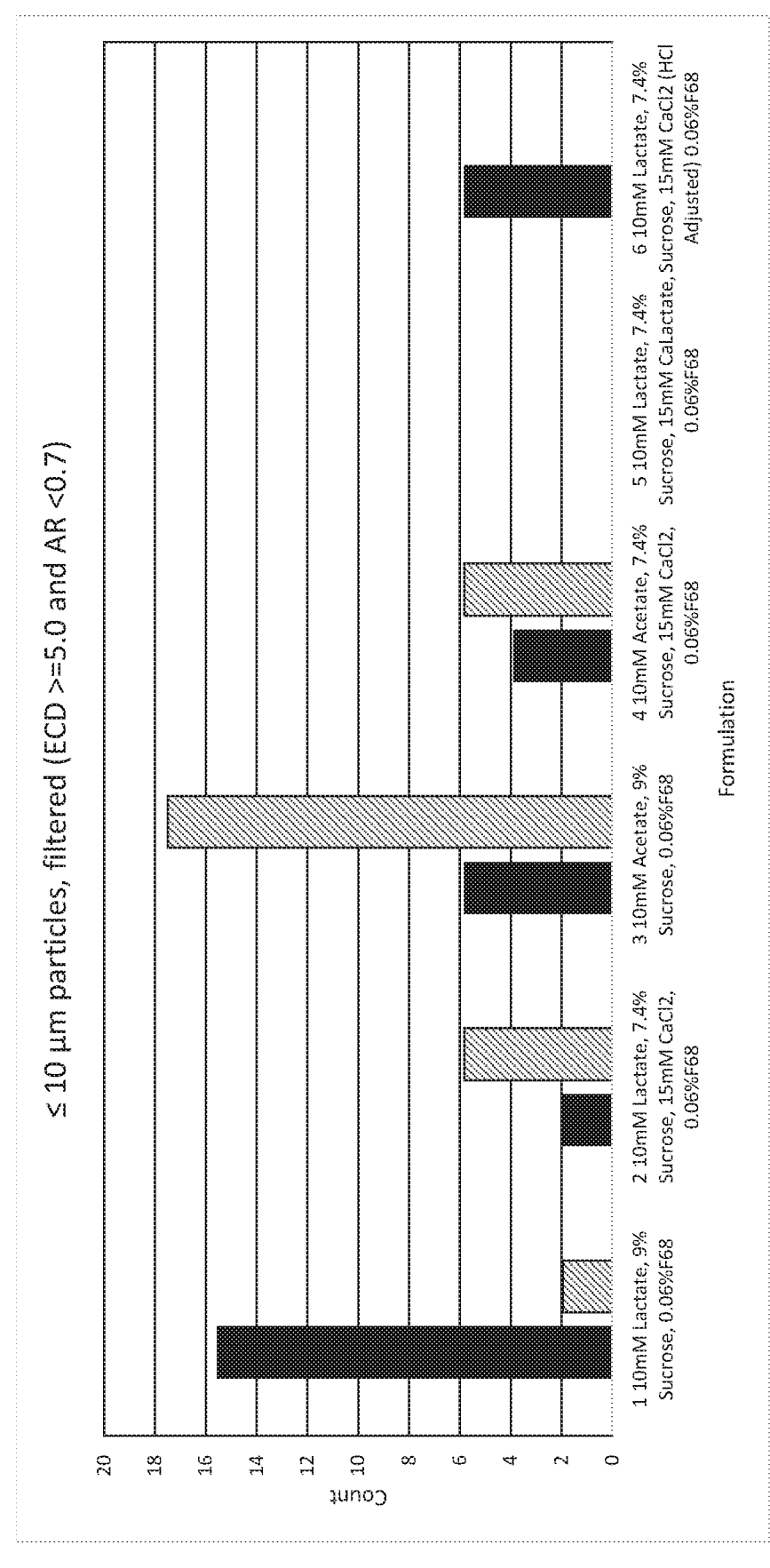
FIG. 20 shows the count of 10 μM sub-visible particles in the adalimumab formulations measured by MFI in Example 7.
Figure 21:
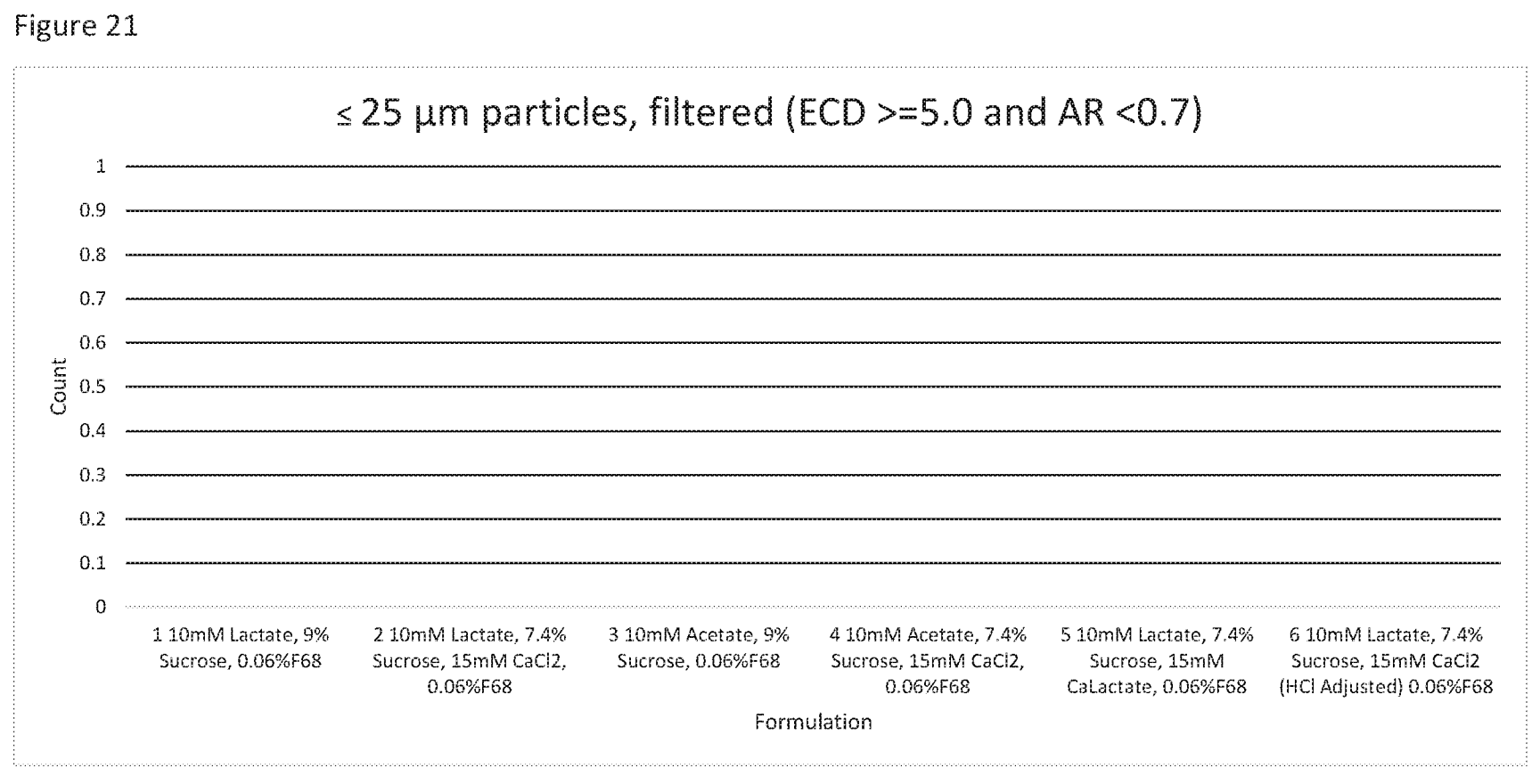

Stability also was assessed by measuring the count of 5 μM, 10 μM, and 25 μM sub-visible particles by MFI in non-transported and transported samples. The particles exhibited an equivalent circular diameter of at least 5.000 and an aspect ratio of less than 0.700. The results are shown in FIGS. 19-21. For the <5 μm particle size, counts were low for all formulations. In addition, upon transport stress, meaningful growth of particles was not observed in formu-

TABLE 10

| | | | | | | | |
|---|---|---|---|---|---|---|---|
| | | | Adalimumab formulations | | | | |
| Ref. | Buffer/pH Adjusting Agent | CaCl₂ (mM) | Excipient | Surfactant | pH | Ab conc. (mg/mL) | Conductivity Osmolality |
| 18A | 10 mM Lactate/Lactic, Ca(OH)₂ | — | 9% sucrose | 0.06% Pluronic F68 | 5.2 | 100 | 0.636 mS/cm 323 mOsm |
| 18B | 10 mM Lactate/Lactic, Ca(OH)₂ | 15 | 7.4% sucrose | 0.06% Pluronic F68 | 5.2 | 100 | 2.851 mS/cm 305 mOsm |
| 18C | 10 mM Acetate/HCl, Ca(OH)₂ | — | 9% sucrose | 0.06% Pluronic F68 | 5.2 | 100 | 0.741 mS/cm 327 mOsm |
| 18D | 10 mM Acetate/HCl, Ca(OH)₂ | 15 | 7.4% sucrose | 0.06% Pluronic F68 | 5.2 | 100 | 2.792 mS/cm 301 mOsm |
| 18E | 10 mM Lactate/Lactic, Ca(OH)₂ | 15 (Calactate) | 7.4% sucrose | 0.06% Pluronic F68 | 5.2 | 100 | 1.373 mS/cm 299 mOsm |
| 18F | 10 mM Lactate/HCl, Ca(OH)₂ | 15 | 7.4% sucrose | 0.06% Pluronic F68 | 5.2 | 100 | 2.914 mS/cm 310 mOsm |

To assess stability, the % acidic peak was measured by CEX-HPLC after 0 days, following transport stress, and after 1 week, 2 weeks and 4 weeks at 4° C., 25° C. and 40° C. The results are shown in FIGS. 7-12. At time zero, samples that were transport-stressed showed similar amounts of % acidic peak compared to the same samples that were not transport-stressed. Small differences were observed in the relative amount of % acidic peak at time zero, however these differences were minor and not considered meaningful from formulation to formulation. Only a small amount of apparent growth was observed after 1 month storage at 4° C., however this is not considered lations 18A, 18E and 18F. At the particle size <10 μm and <25 μm, particle counts were low or particles were not detected.

Example 8: Stabilizing Effects of Lactic Acid

The pH of the VF pool materials containing adalimumab was adjusted to or close to the target pH of pH 5.2 using either hydrochloride acid or lactic acid before DF operation. After OF DF operation, adalimumab is exchanged into the desired composition solution as shown in Table 11 below. The level of High Molecular Weight species present (HMW) the adalimumab compositions was monitored using Size Exclusion Chromatography (SEC). The column used for this assay is a TSK-GEL, G3000SWXL, 5 um particle size, 7.8×300 mm size (Tosoh Bioscience, 08541), with the protein detected at a wavelength of 220 nm, and at a flow rate of 0.5 mL/min. Injection mass loads of protein were 35 μg.

As shown in Table 11, pH adjustment using lactic acid resulted in lower level of HMW, indicating the stabilizing effects of lactic acid.

TABLE 11

| Protein aggregates in adalimumab compositions post UF DF operation | | | |
|---|---|---|---|
| Concen. (mg/mL) | Formulation | HMW % | pH Adjusting Agent |
| 100 | 4% sorbitol, 0.09% PS20 | 1.3 | HCl/NaOH |
| 100 | 4% sorbitol, 0.09% PS20 | 1.1 | HCl/NaOH |
| 100 | 10 mM lactate, 6% sucrose, 0.1% PF68 | 0.81 | HCl/NaOH |
| 100 | 10 mM lactate, 6% sucrose, 0.1% PF68, 15 mM CaCl2 | 0.59 | HCl/NaOH |
| 100 | 10 mM lactate, 6% sucrose, 0.1% PF68, 30 mM CaCl2 | 0.65 | HCl/NaOH |
| 100 | 10 mM lactate, 8.8% sucrose, 0.03% PF68 | 0.39 | lactic acid/ CaOH2 |
| 100 | 10 mM lactate, 7.4% sucrose, 0.03% PF68, 15 mM CaCl2 | 0.41 | lactic acid/ CaOH2 |
| 100 | 10 mM lactate, 6.9% sucrose, 0.03% PF68, 20 mM CaCl2 | 0.41 | lactic acid/ CaOH2 |

All references cited in this application are incorporated by reference herein.

What is claimed is:

1. A method for preparing a purified protein, the method comprises:
   (a) subjecting a sample comprising a protein of interest to a purification process to obtain a preparation comprising the protein of interest,
   (b) conducting a final ultrafiltration and diafiltration operation consisting of (i) adjusting the pH of the preparation produced by step (a) to a target pH using a pH adjusting agent prior to performing the ultrafiltration and diafiltration step, wherein the target pH is from pH 4.0 to pH 7.0, and (ii) performing the final ultrafiltration and diafiltration step in a medium that comprises a buffer, wherein the pH adjusting agent is (A) an acid selected from the group consisting of acetic acid, adipic acid, alginic acid, ascorbic acid, aspartic acid, benzene sulfonic acid, benzoic acid, boric acid, camphorsulfonic acid, caprylic acid, formic acid, glutamic acid, hydrochloride acid, hydrobromic acid, hydroxy acids, hyaluronic acid, methanesulfonic acid, nitric acid, propionic acid, sulfuric acid, sulfonic acid, transexamic acid, and tartaric acid; (B) a base selected from the group consisting of ammonia solution, ammonium carbonate, diethanolamine, calcium hydroxide, ethanolamine, lysine, meglumine, poly-lysine, potassium hydroxide, sodium bicarbonate, sodium borate, sodium carbonate, sodium hydroxide, and triethanolamine; or (C) a buffer selected from the group consisting of acetate buffer, aspartate buffer, ascorbate buffer, borate buffer, benzoate buffer, carbonate buffer, citrate buffer, glycine buffer, HEPES buffer, MOPS buffer, MES buffer, N-(2-acetamido)iminodiacetic acid (ADA) buffer, histidine buffer, lactate buffer, phosphate buffer, succinate buffer, Tris buffer, Bis-tris buffer, and tartrate buffer; and
   (c) recovering a composition comprising the protein from the final ultrafiltration and diafiltration operation, wherein the target pH is within 0.2 pH units of the pH of the composition comprising the protein recovered from the final ultrafiltration and diafiltration operation.

2. The method of claim 1, wherein the acid is selected from the group consisting of lactic acid, malic acid and hyaluronic acid.

3. The method of claim 1, wherein the target pH is from pH 4.0 to pH 6.0.

4. The method of claim 1, wherein the method further comprises concentrating the protein in the preparation to a target concentration.

5. The method of claim 4, wherein the concentrating step is carried out before the pH adjusting step.

6. The method of claim 1, wherein the composition obtained from the final ultrafiltration and diafiltration operation comprises the protein at a concentration of from about 40 mg/ml to about 200 mg/mL.

7. The method of claim 1, wherein the medium comprises a buffer at a concentration of from 2 mM to about 300 mM.

8. The method of claim 1, wherein the medium comprises a buffer at a concentration of from 2 mM to about 10 mM, and wherein the composition obtained from the ultrafiltration and diafiltration operation comprises the protein at a concentration of from about 1 mg/mL to about 50 mg/mL.

9. The method of claim 1, wherein the medium comprises a buffer at a pH outside the buffer capacity range of the buffer, and wherein the composition obtained from the ultrafiltration and diafiltration operation comprises the protein at a concentration of from about 1 mg/mL to about 50 mg/mL.

10. The method of claim 1, wherein the purification process comprises one or more of the following steps: centrifugation, microfiltration, TFF, virus inactivation, affinity chromatography, cation exchange chromatography, anion exchange chromatography, hydrophobic interaction chromatography, ultrafiltration, diafiltration, SPTFF, depth filtration, and mixed-mode chromatography.

11. The method of claim 10, wherein the purification process comprises
   (a) a virus filtration step and one or more of the following steps: centrifugation, microfiltration, TFF, virus inactivation, affinity chromatography, cation exchange chromatography, anion exchange chromatography, hydrophobic interaction chromatography, mixed-mode chromatography, ultrafiltration, diafiltration, SPTFF, and depth filtration, and wherein the preparation is obtained from the virus filtration step;
   (b) a cation exchange chromatography step, and one or more of the following steps: centrifugation, microfiltration, TFF, virus inactivation, affinity chromatography, anion exchange chromatography, hydrophobic interaction chromatography, mixed-mode chromatography, ultrafiltration, diafiltration, SPTFF, virus filtration, and depth filtration, and wherein the preparation is obtained from the cation exchange chromatography step;
   (c) an anion exchange chromatography step, and one or more of the following steps: centrifugation, microfiltration, TFF, virus inactivation, affinity chromatography, cation exchange chromatography, hydrophobic interaction chromatography, mixed-mode chromatography, ultrafiltration, diafiltration, SPTFF, virus filtration, and depth filtration, and wherein the preparation is obtained from the anion exchange chromatography step;

(d) a hydrophobic interaction chromatography step, and one or more of the following steps: centrifugation, microfiltration, TFF, virus inactivation, affinity chromatography, cation exchange chromatography, anion exchange chromatography, mixed-mode chromatography, ultrafiltration, diafiltration, SPTFF, virus filtration, and depth filtration, and wherein the preparation is obtained from the hydrophobic interaction chromatography step; or (e) a mixed-mode chromatography step, and one or more of the following steps: centrifugation, microfiltration, TFF, virus inactivation, affinity chromatography, cation exchange chromatography, anion exchange chromatography, hydrophobic interaction chromatography, ultrafiltration, diafiltration, SPTFF, virus filtration, and depth filtration, and wherein the preparation is obtained from the mixed-mode chromatography step.

12. The method of claim 1, wherein the method further comprises adding a stabilizer to the preparation.

13. The method of claim 12, wherein the stabilizer is one or more selected from: an amino acid, a sugar, a polyol, an anti-oxidant, a chelating agent, a lipid or lipid derivative, a salt, a polymer, an inert protein, a surfactant, and a water-miscible co-solvent.

14. The method of claim 13, wherein
(a) the amino acid is one or more selected from: histidine, arginine, glycine, methionine, alanine, aspartic acid, lysine hydrochloride, proline, lysine, sarcosine, gamma-aminobutyric acid, and glutamic acid;
(b) the anti-oxidant is one or more selected from: ascorbic acid, glutathione, vitamin E, and poly (ethylenimine);
(c) the sugar is one or more selected from: sucrose, trehalose, xylitol, maltose, dextrose, glucose, raffinose, and lactose;
(d) the polyol is one or more of selected from: sugar alcohol, glycerol, erythritol, caprylate, tryptophanate, and sarcosine;
(e) the polymer is one or more selected from: gelatin, hyaluronic acid, polyvinylpyrrolidone (PVP), poly (lactic-co-glycolic acid) (PLGA), polyacrylic acid (PAA), Amphipol A8-35, PAA5-25C8-40C3, polyethylene glycol (PEG), hydroxyethyl (heta) starch, sulfated polysaccharides, polyamino acids, dextran, diethylaminoethyl-dextran, hydroxypropyl-beta-cyclodextrin, sulfobutylether-beta-cyclodextrin, polyethyleneimine (PEI), and carboxymethyl cellulose;
(f) the inert protein is one or more selected from: HSA, BSA and recombinant HA;
(g) the chelating agent is one or more selected from: EDTA, DPTA, citric acid, hexaphosphate, and thioglycolic acid;
(h) the salt is one or more selected from: sodium chloride, sodium sulfate, sodium thiocyanate, potassium chloride, potassium phosphate, calcium lactate, and guanidine hydrochloride;
(i) the surfactant is one or more selected from: polysorbate 20, polysorbate 40, polysorbate 60, polysorbate 80, poloxamer, PEG dodecyl ethers, and PEG tertoctylphenyl ether;
(j) the water-miscible co-solvent is one or more selected from: (DMSO), DMF, DMA and CSA; or
(j) the lipid or lipid derivative is one or more of fatty acids, phospholipids and phospholipid derivatives, DEA phosphate, DEA cetyl phosphate, oleth 10 phosphate, oleth-10, oleth-10 phosphate, DEA cetyl phosphate, mannosylglycerate, polidocanol, sulfobetaine cholate, phospholipids, and C12-15 alcohols benzoate.

15. The method of claim 1, wherein the protein is any one of the following proteins: etanercept, aflibercept, adalimumab, epoetin alfa, darbepoetin alfa, filgrastim, pegfilgrastim, bevacizumab, cetuximab, infliximab, rituximab, eculizumab, trastuzumab, evolocumab, denosumab, romosozumab, erenumab, blinatumomab, and a bispecific T cell engager antibody construct.

16. The method of claim 15, wherein the bispecific T cell engager antibody construct is blinatumomab, anti-CD33 and anti-CD3 bispecific T cell engager antibody construct, anti-EGFRvIII and anti-CD3 bispecific T cell engager antibody construct, anti-DLL3 and anti-CD3 bispecific T cell engager antibody construct, anti-CD19 and anti-CD3 bispecific T cell engager antibody construct, anti-MSLN and anti-CD3 bispecific T cell engager antibody construct, anti-CDH19 and anti-CD3 bispecific T cell engager antibody construct, anti-FLT3 and anti-CD3 bispecific T cell engager antibody construct, anti-DLL3 and anti-CD3 bispecific T cell engager antibody construct, anti-CDH3 and anti-CD3 bispecific T cell engager antibody construct, anti-CD70 and anti-CD3 bispecific T cell engager antibody construct, anti-PSMA and anti-CD3 bispecific T cell engager antibody construct, and anti-BCMA and anti-CD3 bispecific T cell engager antibody construct.

17. The method of claim 1, wherein the ultrafiltration and diafiltration operation is carried out at a temperature of from about 25° C. to about 50° C.

18. The method of claim 17, wherein the ultrafiltration and diafiltration operation is carried out at a temperature from about 25° C. to about 40° C.

19. The method of claim 18, wherein the ultrafiltration and diafiltration operation is carried out at a temperature from about 30° C. to about 40° C.

20. The method of claim 1, wherein the composition obtained from the final ultrafiltration and diafiltration operation is more stable compared to a composition prepared by the same method without the pH adjusting step.

21. The method of claim 1, wherein the protein is etanercept.

22. The method of claim 1, wherein the protein is aflibercept.

23. The method of claim 1, wherein the protein is adalimumab.

24. The method of claim 1, wherein the target pH is pH 5.0 to pH 7.0.

25. A method for preparing a purified protein, the method comprises:
(a) subjecting a sample comprising a protein of interest selected from etanercept, aflibercept, and adalimumab to a purification process to obtain a preparation comprising the protein of interest,
(b) conducting a final ultrafiltration and diafiltration operation consisting of (i) adjusting the pH of the preparation produced by step (a) to a target pH prior to performing the ultrafiltration and diafiltration step, and (ii) performing the final ultrafiltration and diafiltration step, and
(c) recovering a composition comprising the protein from the final ultrafiltration and diafiltration operation, wherein the target pH is within 0.2 pH units of the pH of the composition comprising the protein recovered from the final ultrafiltration and diafiltration operation.

26. The method of claim 25, wherein the pH is adjusted using a pH adjusting agent.

27. The method of claim 26, wherein the pH adjusting agent is an acid selected from the group consisting of acetic acid, adipic acid, alginic acid, ascorbic acid, aspartic acid, benzene sulfonic acid, benzoic acid, boric acid, camphorsulfonic acid, caprylic acid, formic acid, glutamic acid, hydrochloride acid, hydrobromic acid, hydroxy acids, hyaluronic acid, methanesulfonic acid, nitric acid, phosphoric acid, propionic acid, sulfuric acid, sulfonic acid, transexamic acid, and tartaric acid.

28. The method of claim 26, wherein the pH adjusting agent is a base selected from the group consisting of ammonia solution, ammonium carbonate, diethanolamine, calcium hydroxide, ethanolamine, lysine, meglumine, polylysine, potassium hydroxide, sodium bicarbonate, sodium borate, sodium carbonate, sodium hydroxide, and triethanolamine.

29. The method of claim 25, wherein the target pH is from about pH 4.0 to about pH 7.0.

30. The method of claim 29, wherein the target pH is from about pH 4.0 to about pH 6.0.

31. The method of claim 29, wherein the target pH is pH 5.0 to pH 7.0.

32. The method of claim 25, wherein the method further comprises concentrating the protein in the preparation to a target concentration.

33. The method of claim 32, wherein the concentrating step is carried out before the pH adjusting step.

34. The method of claim 25, wherein the composition obtained from the final ultrafiltration and diafiltration operation comprises the protein at a concentration of from about 40 mg/ml to about 200 mg/mL.

35. The method of claim 25, wherein the purification process comprises one or more of the following steps: centrifugation, microfiltration, TFF, virus inactivation, affinity chromatography, cation exchange chromatography, anion exchange chromatography, hydrophobic interaction chromatography, ultrafiltration, diafiltration, SPTFF, depth filtration, and mixed-mode chromatography.

36. The method of claim 25, wherein the method further comprises adding a stabilizer to the preparation.

37. The method of claim 36, wherein the stabilizer is one or more selected from: an amino acid, a sugar, a polyol, an anti-oxidant, a chelating agent, a lipid or lipid derivative, a salt, a polymer, an inert protein, a surfactant, and a water-miscible co-solvent.

38. The method of claim 37, wherein (a) the amino acid is one or more selected from: histidine, arginine, glycine, methionine, alanine, aspartic acid, lysine hydrochloride, proline, lysine, sarcosine, gamma-aminobutyric acid, and glutamic acid;

(b) the anti-oxidant is one or more selected from: ascorbic acid, glutathione, vitamin E, and poly (ethylenimine);

(c) the sugar is one or more selected from: sucrose, trehalose, xylitol, maltose, dextrose, glucose, raffinose, and lactose;

(d) the polyol is one or more of selected from: sugar alcohol, glycerol, erythritol, caprylate, tryptophanate, and sarcosine;

(e) the polymer is one or more selected from: gelatin, hyaluronic acid, polyvinylpyrrolidone (PVP), poly (lactic-co-glycolic acid) (PLGA), polyacrylic acid (PAA), Amphipol A8-35, PAA5-25C8-40C3, polyethylene glycol (PEG), hydroxyethyl (heta) starch, sulfated polysaccharides, polyamino acids, dextran, diethylaminoethyl-dextran, hydroxypropyl-beta-cyclodextrin, sulfobutylether-beta-cyclodextrin, polyethyleneimine (PEI), and carboxymethyl cellulose;

(f) the inert protein is one or more selected from: HSA, BSA and recombinant HA;

(g) the chelating agent is one or more selected from: EDTA, DPTA, citric acid, hexaphosphate, and thioglycolic acid;

(h) the salt is one or more selected from: sodium chloride, sodium sulfate, sodium thiocyanate, potassium chloride, potassium phosphate, calcium lactate, and guanidine hydrochloride;

(i) the surfactant is one or more selected from: polysorbate 20, polysorbate 40, polysorbate 60, polysorbate 80, poloxamer, PEG dodecyl ethers, and PEG tertoctylphenyl ether;

(j) the water-miscible co-solvent is one or more selected from: (DMSO), DMF, DMA and CSA; or (j) the lipid or lipid derivative is one or more of fatty acids, phospholipids and phospholipid derivatives, DEA phosphate, DEA cetyl phosphate, oleth 10 phosphate, oleth-10, oleth-10 phosphate, DEA cetyl phosphate, mannosylglycerate, polidocanol, sulfobetaine cholate, phospholipids, and C12-15 alcohols benzoate.

39. The method of claim 25, wherein the ultrafiltration and diafiltration operation is carried out at a temperature of from about 25° C. to about 50° C.

40. The method of claim 25, wherein the final ultrafiltration and diafiltration operation is carried out using a medium that comprises essentially no buffer.

41. The method of claim 40, wherein the protein is etanercept or aflibercept.

42. The method of claim 25, wherein the final ultrafiltration and diafiltration operation is carried out in a medium that comprises a buffer.

43. The method of claim 42, wherein the protein is adalimumab.

* * * * *